(12) United States Patent
Takaoka et al.

(10) Patent No.: US 7,737,859 B2
(45) Date of Patent: Jun. 15, 2010

(54) PSYCHOSOMATIC STATE DETERMINATION SYSTEM

(75) Inventors: Michiko Takaoka, Tokyo (JP);
Kakuichi Shiomi, Tokyo (JP)

(73) Assignee: Electronic Navigation Research Institute, an Independent Administrative Institution, Tokyo (JP)

( * ) Notice: Subject to any disclaimer, the term of this patent is extended or adjusted under 35 U.S.C. 154(b) by 522 days.

(21) Appl. No.: 10/546,475

(22) PCT Filed: Feb. 23, 2004

(86) PCT No.: PCT/JP2004/002054

§ 371 (c)(1),
(2), (4) Date: Apr. 21, 2006

(87) PCT Pub. No.: WO2004/082479

PCT Pub. Date: Sep. 30, 2004

(65) Prior Publication Data
US 2006/0232430 A1 Oct. 19, 2006

(30) Foreign Application Priority Data
Feb. 24, 2003 (JP) ............................ 2003-046428

(51) Int. Cl.
*G08B 23/00* (2006.01)
(52) U.S. Cl. .................... 340/575; 340/573.1; 600/595; 709/227
(58) Field of Classification Search ............... 340/575, 340/573.1; 600/595; 709/227
See application file for complete search history.

(56) References Cited

U.S. PATENT DOCUMENTS

| 5,311,877 | A | * | 5/1994 | Kishi | 600/545 |
| 5,422,479 | A | * | 6/1995 | Sahori | 250/231.18 |
| 5,458,137 | A | * | 10/1995 | Axe et al. | 128/204.23 |
| 6,134,731 | A | * | 10/2000 | Thom et al. | 5/662 |
| 6,511,424 | B1 | * | 1/2003 | Moore-Ede et al. | 600/300 |
| 6,658,287 | B1 | * | 12/2003 | Litt et al. | 600/544 |
| 6,821,258 | B2 | * | 11/2004 | Reed et al. | 600/595 |
| 7,321,842 | B2 | | 1/2008 | Shiomi et al. | |
| 7,363,226 | B2 | | 4/2008 | Shiomi et al. | |
| 7,407,484 | B2 | * | 8/2008 | Korman | 600/300 |
| 2002/0156392 | A1 | * | 10/2002 | Arai et al. | 600/546 |
| 2008/0132768 | A1 | | 6/2008 | Shiomi et al. | |

FOREIGN PATENT DOCUMENTS

JP 1-207036 8/1989

(Continued)

*Primary Examiner*—Davetta W Goins
*Assistant Examiner*—Ojiako Nwugo
(74) *Attorney, Agent, or Firm*—Finnegan, Henderson, Farabow, Garrett & Dunner, L.L.P.

(57) ABSTRACT

The present invention provides a psychosomatic state determination system 1 for the purpose of predicting or determining the psychosomatic state of a subject without imparting any awareness to the subject, comprising a data processing means 20 for calculating a psychosomatic state exponent such as Lyapunov exponent from the time series signal of a load value or a barycentric position of the subject, and an evaluation means 22 for comparing the temporal tendency of a psychosomatic state exponent calculated in said data processing means with the temporal tendency of a known psychosomatic state exponent corresponding to a psychosomatic state to thereby predict the psychosomatic state of the subject.

18 Claims, 10 Drawing Sheets

FOREIGN PATENT DOCUMENTS

| | | |
|---|---|---|
| JP | 4-28353 A | 1/1992 |
| JP | 8-586 A | 1/1996 |
| JP | 9-109723 | 4/1997 |
| JP | 10-146321 A | 6/1998 |
| JP | 11-161798 | 6/1999 |
| JP | 11-332856 A | 12/1999 |
| JP | 2001-283134 A | 10/2001 |
| JP | 2001-344341 A | 12/2001 |
| JP | 2002-165799 A | 6/2002 |
| JP | 2003-144438 A | 5/2003 |

* cited by examiner (a)

(b)

PSYCHOSOMATIC STATE DETERMINATION SYSTEM

TECHNICAL FIELD

The present invention is related to a psychosomatic state determination system for measuring a time series signal of a load value or a barycentric position of a human being without imparting any awareness to a subject and predicting or determining the psychosomatic state such as wakeful or non-wakeful state of a subject.

BACKGROUND ART

Hitherto, there has been provided a system for determining a doze state, for preventing accidents caused by the doze and the like of a driver of automobiles or railway cars, a pilot of an air-craft or an operator of a flight control machine, from the tilt of head or the number of blinking times of the driver(for example, see patent reference #1 and #2).

In addition, there has been provided a system for sounding an alarm or for activating an automatic brake, by regarding as a doze if the duration of no-operation exceeds a predetermined period of time or a sensor placed in a specific location on an operating console is not touched for a predetermined period of time.

Patent Reference #1
  JP-A-11-161798 (pp. 2-3, paragraphs 7 to 12; pp. 5, paragraphs 36 to 37)

Patent Reference #2
  JP-A-9-109723 (pp. 5, paragraph 50)

In the system disclosed in such references as mentioned above, because the tilt of head or the number of blinking times to be determined has a considerable variation among individuals, the determination of doze is often entrusted to a subjective decision, resulting in a difficulty in making an accurate determination, and it has been impossible to distinguish a state immediately prior to doze from a sufficiently wakeful state, leading to a problem that it was not possible to completely accommodate the prevention of accidents.

In addition, because sensors or cameras are needed to be put on to or in the vicinity of the driver's body, there are disadvantages that the device needs a significant effort to be put on and taken off, that the installed device is a hindrance for driving or piloting and that the device is a distraction.

The system for sounding an alarm or operating an automatic brake if no operation is done for a predetermined period of time may misread that the driver is dozing although he or she is not, when the duration of no-operation has been accidentally prolonged, requiring the subject has to drive while always paying attention to do some operation posing a problem that the system tends to induce an accident on the contrary.

The setting of the period of time for the detection of doze is after all performed often based on a subjective decision; therefore an accurate determination of psychosomatic state was unlikely to be achieved.

SUMMARY OF THE INVENTION

The inventors of the present invention have invented, in light of the above problems, a psychosomatic state determination system which makes it possible to predict or determine the psychosomatic state of a subject without imparting any awareness or burden of the determination to the subject and without relying on a subjective determination and to prevent an accident with certainly and before it happens and before the subject falls into a doze by calculating psychosomatic state exponents, such as Lyapunov exponents, from a time series signal of a load value or a barycentric position of a human being presenting chaotic behavior, and by comparing it with a known psychosomatic state exponent.

The term "psychosomatic state" used in the present invention refers to a health condition of a body and a psychological state. For example, the health condition includes a wakeful state where he or she is "awakened", and a non-wakeful state where he or she is "sleeping", and in addition thereto, the non-wakeful state is further classified into several levels from a restless sleep (REM sleep) to a deep sleep (non-REM sleep). The psychological state includes a state represented by expressions such as fatigue, tension, fear and the like. Since the health state of a body and psychological state both originate from the cerebral functions and have a close relationship, these state are termed collectively as a "psychosomatic state". As the psychosomatic state originates from the cerebral functions, the "psychosomatic state" in the present invention is used as a synonym of a "cerebral function state".

The chaos theory, as documented in typical known references including "The essence of chaos" by E. N. Lorenz, means "a theory for seeking the dependency and the like to the initial conditions from the stochastic oscillation phenomenon and the like occurring in a nonlinear system", and the "psychosomatic state exponents such as Lyapunov exponents" mean numerical values for quantitatively determining whether or not it is a chaos in the chaos theory.

The load value of a human being includes a value conversable to the load value or a value obtained with respect to the load value (such as an acceleration value).

The invention in accordance with claim 1 provides a psychosomatic state determination system for predicting a psychosomatic state such as a wakeful state and a non-wakeful state of a subject, comprising: a data processing means for calculating a psychosomatic state exponent such as Lyapunov exponent from a time series signal of a load value or a barycentric position of a subject; and an evaluation means for comparing a temporal tendency of a psychosomatic state exponent calculated in said data processing means with a temporal tendency of a known psychosomatic state exponent corresponding to a psychosomatic state to thereby predict a psychosomatic state of said subject.

The invention in accordance with claim 2 provides a psychosomatic state determination system for determining a psychosomatic state such as a wakeful state and a non-wakeful state of a subject, comprising: a data processing means for calculating a psychosomatic state exponent such as Lyapunov exponent from a time series signal of a load value or a barycentric position of a subject; and an evaluation means for comparing a value of psychosomatic state exponent calculated in said data processing means with a value of a known psychosomatic state exponent corresponding to a psychosomatic state to thereby determine a psychosomatic state of said subject.

In accordance with the invention set forth in either claim 1 or 2, the psychosomatic state of the subject can be predicted or determined without imparting any awareness to the subject and without depending on any subjective decision.

The invention in accordance with claim 3 provides a psychosomatic state determination system, comprising a sensor for outputting a load value of said subject.

In accordance with the invention set forth in claim 3, by using a sensor for outputting the load value, it is possible to predict or determine the psychosomatic state without imparting any awareness to the subject.

The invention in accordance with claim 4 provides a psychosomatic state determination system wherein said sensor is one single unit.

In accordance with the invention set forth in claim 4, the consideration about the synchronization among a plurality of sensors or about the difference among individuals caused by the output delays occurred among sensors is not needed, and furthermore the cost of parts can be saved.

The invention in accordance with claim 5 provides a psychosomatic state determination system, wherein said sensor is either a pressure sensor, such as a piezoelectric element, a pressure-sensitive resistor element and a potentiometer, or an acceleration sensor.

The sensor that outputs a load value as described above is compact, has a high pressure resistance, and is easily available, and can be built into a chair or a bed for being easily used for the psychosomatic state determination.

The invention in accordance with claim 6 provides a psychosomatic state determination system, wherein said sensor is attached to a chair or a bed to which a load of said subject is applied.

In accordance with the invention set forth in claim 6, the psychosomatic state determination can be conducted with a sensor being attached to a chair or a bed and with the subject being on the seat or lying on the bed.

The invention in accordance with claim 7 provides a psychosomatic state determination system, wherein said chair or bed has an elastic material such as a spring therein.

In accordance with the invention set forth in claim 7 the chair or bed has less sense of incongruity the subject and the sensor can be built in directly, eliminating the need of installing the sensor under the floor.

The invention in accordance with claim 8 provides a psychosomatic state determination system, comprising a noise elimination means for eliminating an unwanted frequency component included in a time series signal of a load value or a barycentric position of said subject.

In accordance with the invention set forth in claim 8 the prediction or determination has its precision improved by removing unnecessary frequency components from the time series signal of the load value or barycentric position.

The invention in accordance with claim 9 provides a psychosomatic state determination system, wherein said system extracts samples from a time series signal of a load value or a barycentric position of said subject at a frequency of from 10 Hz to 100 Hz.

In accordance with the invention set forth in claim 9 the time series signal with the frequency required for the chaotic analysis can be extracted, and even with less number of samples the same effect as monitoring continuously the psychosomatic state can be obtained. In addition, by limiting to the time series signal having periodicity, the signal processing or the calculation of psychosomatic state in a much together manner can be achieved.

The invention in accordance with claim 10 provides a psychosomatic state determination system, wherein said system comprises an amplifying means for amplifying a time series signal of a load value or a barycentric position of said subject.

In accordance with the invention set forth in claim 10 the data processing can be facilitated by the amplification of the time series signal of the load value or barycentric position when the signal is small.

The invention in accordance with claim 11 provides a psychosomatic state determination system, wherein said system comprises a calculation means for calculating a barycentric position of said subject from each of load values output from a plurality of said sensors.

In accordance with the invention set forth in claim 11 the barycentric position can be determined from not less than two sensors.

The invention in accordance with claim 12 provides a psychosomatic state determination system, wherein said system comprises a warning means for sounding an alarm by using a display and/or a speaker to said subject or for communicating to an administration station which manages said subject, based on a psychosomatic state predicted or determined of said subject.

In accordance with the invention set forth in claim 12 the prediction or determination result of the psychosomatic state of subject is communicated to the management station of the subject or directly to the subject to thereby prevent an accident with certainly and before it happens.

The invention in accordance with claim 13 provides a psychosomatic state determination system, wherein said system comprises an action detection means for detecting in time sequence an operation status or a driving behavior of said subject: and wherein said evaluation means compares a temporal tendency and/or a value of a known psychosomatic state exponent corresponding to a status detected in said action detection means and a psychosomatic state with a temporal tendency and/or a value of said calculated psychosomatic exponent to thereby predict or determine a psychosomatic state for each of said states of said subject.

In accordance with the invention set forth in claim 13 successive prediction or determination in correspondence with the status can be conducted since the psychosomatic state exponents may vary according to the circumstances where the subject is residing.

The invention in accordance with claim 14 provides a psychosomatic state determination system, wherein said system comprises a stimuli outputting means for giving to said subject a stimulus such as a physical stimulus or an audio-visual stimulus; and wherein said evaluation means compares a temporal tendency and/or a value of a known psychosomatic state exponent at a time when said stimulus is output from said stimulus outputting means with a temporal tendency and/or a value of said calculated psychosomatic state exponent to thereby predict or determine a psychosomatic state for each of said states of said subject.

In accordance with the invention set forth in claim 14, by supplying an intentional stimulation to the subject, it is also possible to predict or determine the psychosomatic state of the subject at that time.

The invention in accordance with claim 15 provides a psychosomatic state determination system, wherein said stimuli outputting means promotes a change in a behavior of said subject by outputting said stimulus effective for preventing from falling into an abnormal psychosomatic state from said stimuli outputting means based on a psychosomatic state predicted or determined of said determinee.

In accordance with the invention set forth in claim 15 by supplying an intentional stimulation to the subject, it is possible to prevent the subject from falling into an abnormal psychosomatic state or to facilitate a change in the behavior of the subject.

Reference Numerals
   1: psychosomatic state determination system
   2: psychosomatic state evaluation means
  20: data processing means
  22: evaluation means
  24: exponent database 3: sensor
32: differential amplifier
34: analog-to-digital converter
4: noise elimination means
5: warning means
6: subject
7: chair
8: elastic material
9: managing station
10: speaker
11: display
12: action detection means
13: stimuli outputting means
15: stimuli database

BEST MODE FOR CARRYING OUT THE INVENTION

Figure 1:
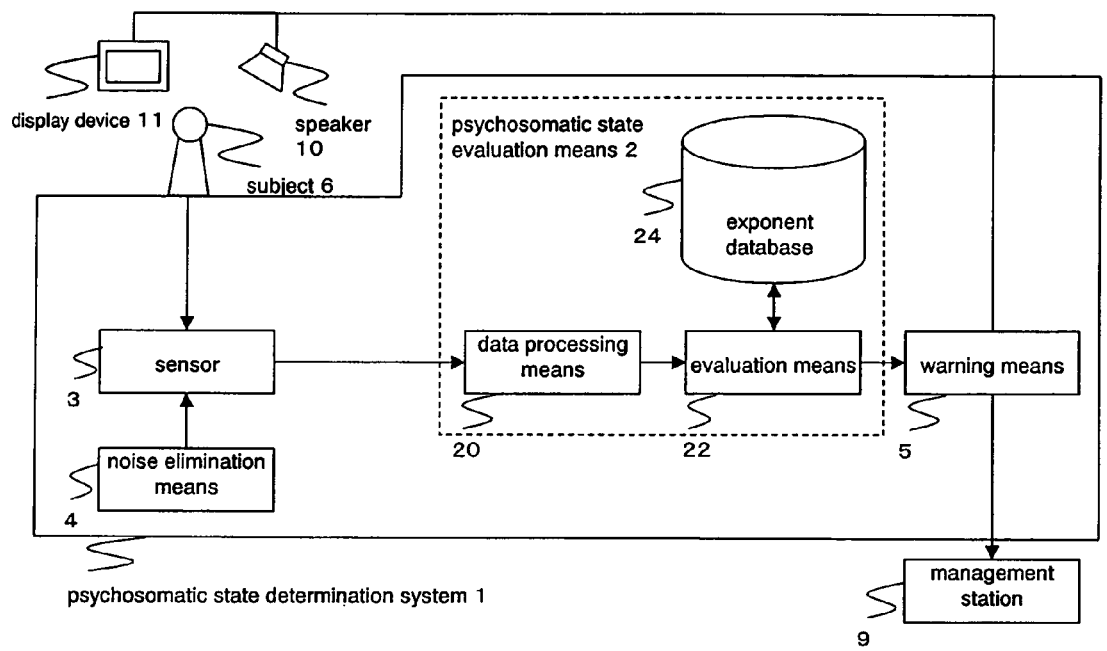
FIG. 1 shows an exemplary system configuration of the psychosomatic state determination system in accordance with the present invention.

Now an exemplary embodiment of the present invention will be described in greater details with reference to accompanying drawings. FIG. 1 shows an exemplary system configuration of a psychosomatic state determination system 1 in accordance with the present invention. The psychosomatic state determination system 1 includes a psychosomatic state evaluation means 2, a sensor 3, a noise elimination means 4, and a warning means 5.

The psychosomatic state evaluation means 2 is a means for predicting or determining the psychosomatic state of a subject 6 from the time series signal of the load value or barycentric position of the subject 6.

The temporal change of a load value or barycentric position is known to be caused by the body movement derived from the result of the information processing by the brain. The load value or barycentric position of a human being at any given moment is a result of combination of the instruction transfer signal from the brain to a body part such as the heart, hands and legs, with the delay portion of respective instruction, and the inventors of the present invention have found that the psychosomatic state can be determined or in some cases predicted by chaos theoretically analyzing the temporal change of a load value or a barycentric position.

For example, the brain of a human being in a sufficient wakefulness state effectively processes infinite number of pieces of incoming information from outside; the barycentric position in such the case shows a chaos theoretically stable trace.

The collective term of a stable solution having the characteristic of attracting the trace, namely a set where the trace asymptotes is called an attractor, and the attractor which indicates a chaos is referred to as a strange attractor, because of its geometrically complex structure.

On the other hand, when falling into a doze and the like by fatigue, the brain accepts only a fraction of incoming information from outside; the movement of the barycentric position in such a case is mechanical. This mechanical movement shows an attractor that has a simpler trace when compared with a strange attractor in the above-cited wakeful state; however this attractor behaves unstably in response to the disturbance ab extra.

The load value of the subject 6 required for the psychosomatic state evaluation means 2 includes the load value applied to the pressure sensor or a value conversable to the load value or a value obtained corresponding to the load value (for example, an acceleration value) and the data may be of one dimensional, or multi-dimensional. Also the number of dimensions has no concern to the barycentric position.

The psychosomatic state evaluation means 2 has a data processing means 20, an evaluation means 22 and an exponent database 24.

The data processing means 20 is a means for calculating the psychosomatic state exponent from the time series signal of the load value or barycentric position of the subject 6.

The psychosomatic state exponent is a value providing a basis for the prediction or determination of the psychosomatic state. More specifically, this exponent is Lyapunov exponent and the like used for the chaotic exponent, meaning the value with which it is possible to quantitatively determine whether or not a chaos in the chaos theory or the temporal mean value thereof. The psychosomatic state exponent is different from other exponent that has a variation among individuals of not less than several hundred percent, such as steroids in the blood or sputum, and has much less variation among individuals and is an exponent calculated for each of psychosomatic states, such as the number of heart beats and the blood pressure.

Furthermore, the psychosomatic state may not be limited to the conventional Lyapunov exponent, but may be a cerebral function exponent as will be described later.

The cerebral function exponent is an exponent for evaluating the chaoticity, similarly to the Lyapunov exponent in the prior art. The value is calculated by restricting the object of calculation to the time series signal that has a strong periodicity or periodic characteristic (the frequency analysis thereof should generate a spectrum with explicit peaks on the frequency domain) such as the time series signal of the load value or barycentric position of the subject 6 or the time series signal of the continuous speech voice.

In addition, in case of the cerebral function exponent, in its calculation process, a neighborhood points set is generated by previously cutting out a processing unit based on the periodicity of the time series signal, thus it is a psychosomatic state exponent capable of being calculated in a more stable and fast manner than the conventional Lyapunov exponent. Therefore the prediction or determination of the psychosomatic state can be conducted in a more immediate and accurate manner, and is effective in a situation where the human error due to a doze and the like must be prevented with certainly.

The evaluation means 22 is a means for predicting or determining the psychosomatic state of the subject 6 based on the result of comparison of the psychosomatic state exponent calculated in the data processing means 20 with the known psychosomatic state exponent that has been stored in the exponent database 24.

The exponent database 24 stores the temporal tendency and/or numerical value of the time series signal corresponding to a specific psychosomatic state. For instance, the exponent is stored as a value or tendency of the time series signal for a standing human being who is wakeful, or as a value or a tendency of the time series signal for a sitting human being who is tired. The temporal tendency is also a temporal change (gradient) of the psychosomatic state exponent, which can be expressed by a number, a positive or negative symbol, a ratio and the like. Since the psychosomatic state exponent is calculated from the time series signal of the load value or barycentric position of the subject 6, the psychosomatic state can be predicted or determined without imparting any awareness to the subject 6, without based on any subjective decision. As has been described above, since the psychosomatic state exponent has less variation among individuals, it is not needed to previously experiment or measure each subject to store the psychosomatic state exponents of each individual.

Now take an example where the time series signal of the load value to the ground of a subject 6 standing still is measured to thereby predict or determine the psychosomatic state. If the subject 6 is tired, he or she will shake his or her body larger due to somnolence and the time series signal of the load value will become unstable and random, then the psychosomatic state exponent at this time increases when compared with the wakeful state.

From the temporal tendency that it is increasing, not a subjective but an objective prediction can be made that the subject 6 is going to fall asleep, and not a subjective but an objective prediction can be made that the subject is in sleep when it settles to a certain value.

The sensor 3 may be any sensor which can output the load value of the subject 6, a value conversable to the load value, or a value obtained in correspondence with the load value. For example, the sensor 3 includes various sensors such as a sensor such as a weight scale for weighing, a potentiometer in which the resistance varies in linear relation to the pressure due to the pressure-sensitive resistor element, a sensor which generates an electromotive force by means of a combination of a coil and a magnet, a sensor such as a piezoelectric element which outputs electric signals relative to the pressure, a sensor of static capacitance type, an acceleration sensor which outputs the acceleration value. More specifically, the sensor may be any one of a pressure sensor, a strain sensor, a displacement sensor, or an acceleration sensor and the like.

A typical example of the sensor 3 is the FSR series pressure-sensitive resistor element available from Interlink Electronics Corp.

For measuring the barycentric position, output values of not less than two sensors 3 such as pressure sensors are mutually compared with one another to thereby identity the barycentric position.

There are cases where a trimmer or a volume is provided for adjusting the signal level of the sensor output.

The sensor 3 of this form is compact, has an improved pressure resistance, and is easily available, so that it can be built in to the seating surface or backrest of a chair, or a bed and the like, making it possible to measure the load value or barycentric position without imparting any awareness to the subject 6.

In order to predict or determine the psychosomatic state of the subject 6, the signal obtained form the sensor 3 may be of one dimension as have been described above, in other words only one single sensor is required for the prediction or determination of the psychosomatic state from the time series signal of the load value.

There is an advantage that, with only one single sensor, any consideration is not needed with respect to the synchronization among a plurality of sensors when measuring the barycentric position and the like using not less than two sensors, as well as with respect to the variation among individuals due to the output delay present among sensors, and that less number of parts is required.

Figure 4:
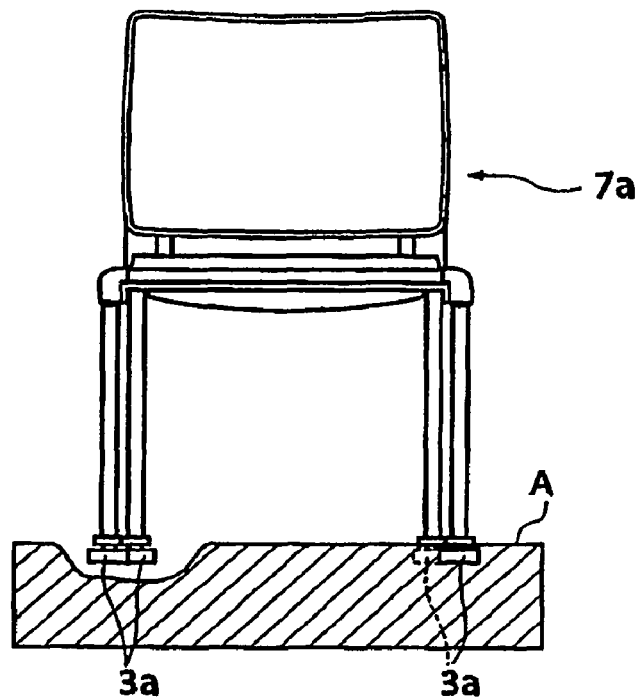
FIG. 4 shows an exemplary chair having a sensor attached thereto.
Figure 4:
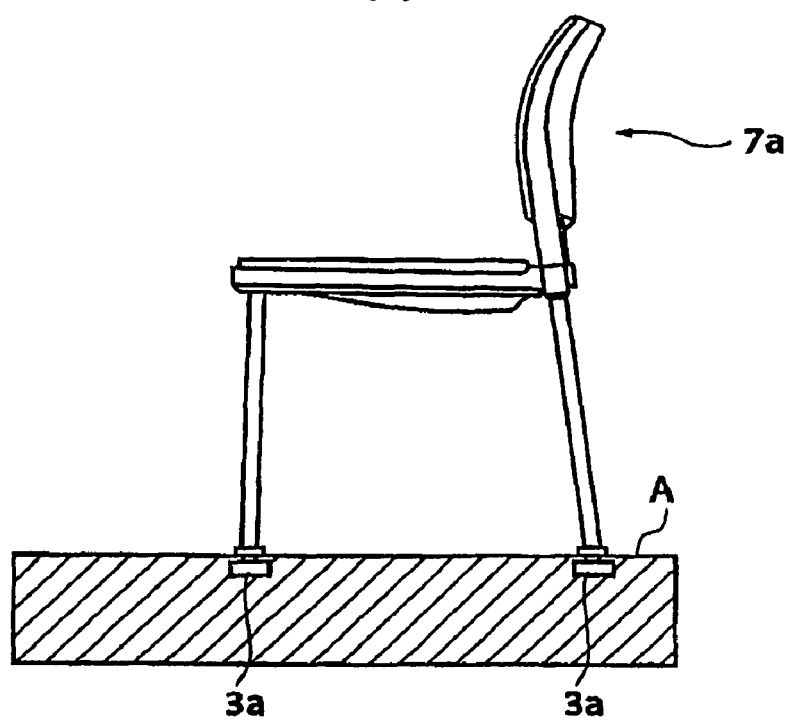
Figure 5:
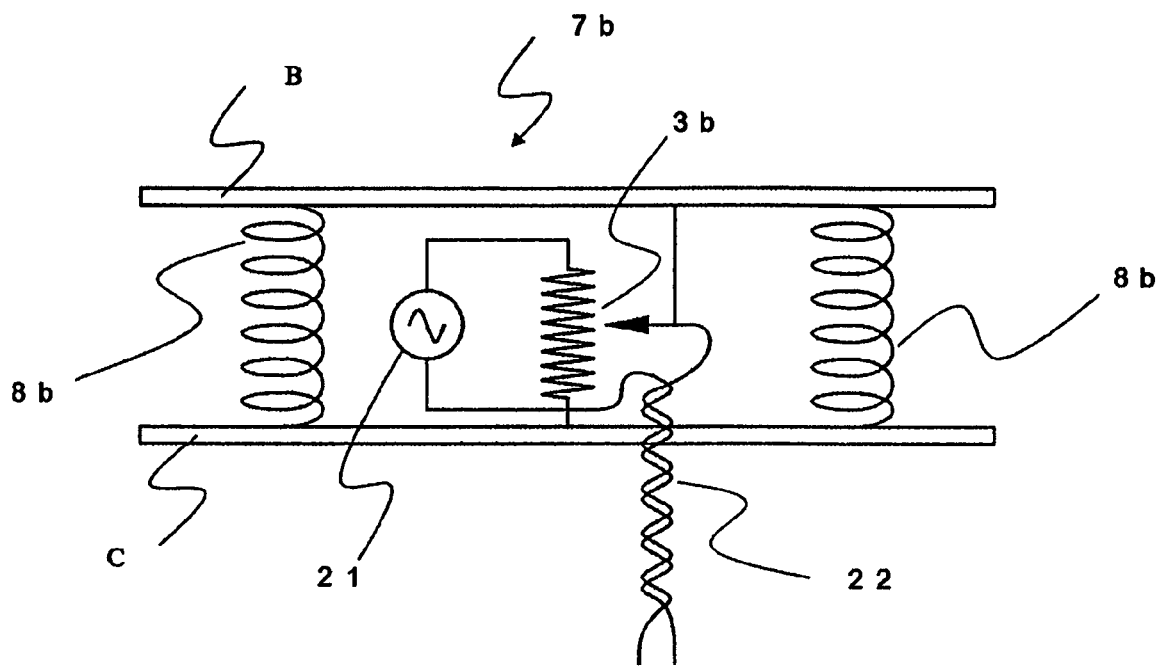
FIG. 5 shows another exemplary chair having a sensor attached thereto.
Figure 6:
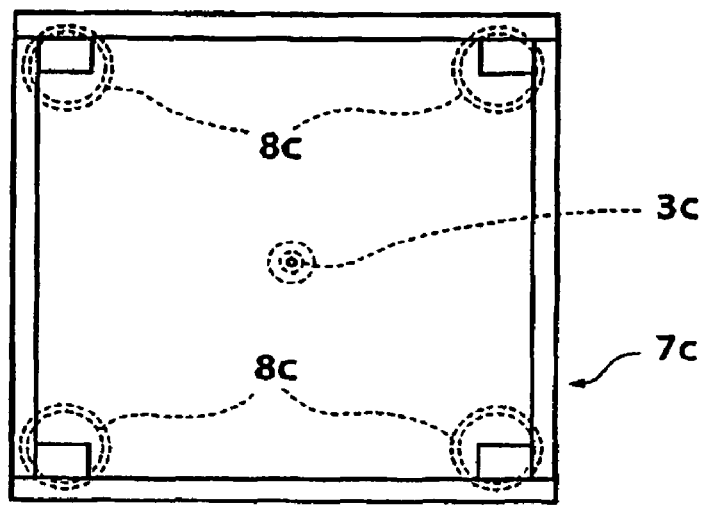
FIG. 6 shows still another exemplary chair having a sensor attached thereto.
Figure 6:
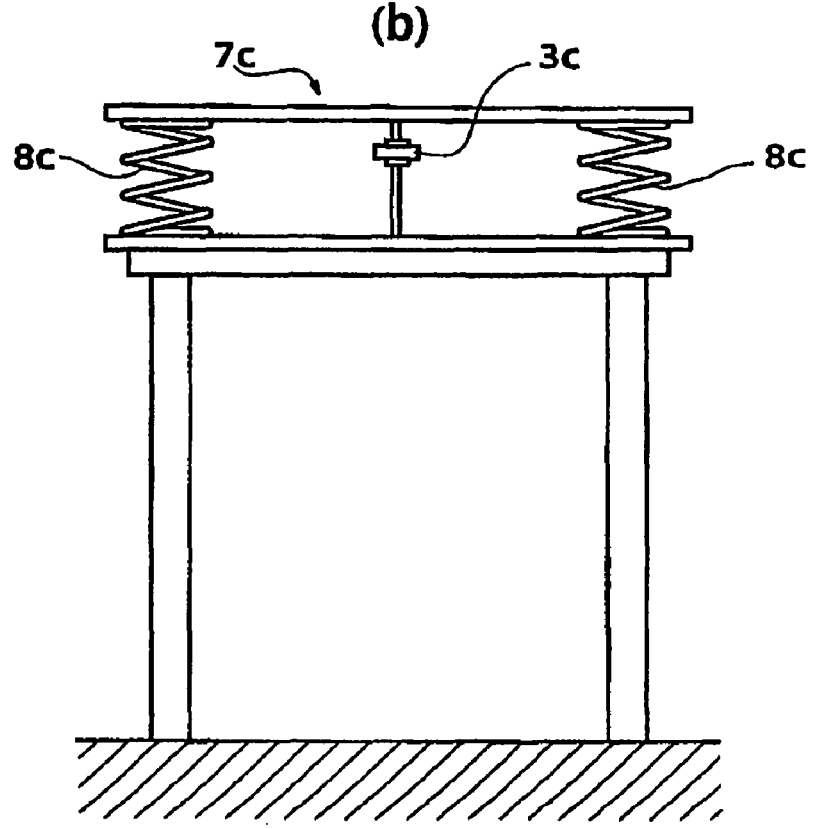

A concrete example of the prediction or determination of the psychosomatic state from the load value of the subject applied to a chair after installing a sensor to a chair is shown in FIGS. 4 to 6. FIG. 4 shows a front view (a) and a side view (b) of a chair 7a, which has four pressure sensors attached as sensor 3a under the legs, and the sensors 3a are hidden under the floor surface A. Either the chaotic analysis of the time series signal of the output vale from each of the sensors 3a, or the calculation of the barycentric position of the subject from the output values of all four sensors 3a followed by the chaotic analysis of the time series signal of thus obtained barycentric position makes it possible to predict or determine the psychosomatic state of the subject.

FIG. 5 and FIG. 6 show an exemplary case in which an elastic material 8 such as a spring is inserted under the seat surface of a chair 7 to thereby measure the change in resistance caused by the stretch and distortion of the elastic material 8 by using a sensor 3 such as a potentiometer.

In FIG. 5, between the loading surface B and the installation surface C of a chair 7b, there are an elastic material 8b and a sensor 3b inserted therebetween, the power supply 21 for driving the sensor 3b is placed, and signal lines 22 including a power line are wired to the external psychosomatic state evaluation means 2.

From FIG. 6(a), taken from the top of the chair 7c shown in FIG. 6(b), it can be seen that elastic materials 8c are nipped on four corners of the chair 7c and a sensor 3c is placed on the center of the chair 7c.

With the elastic material 8, the chair 7 provides less sense of discomfort when the subject sits down thereon, the sensor 3 can be inserted in the chair 7 directly, and therefore no sensor 3 is required to be placed on the leg of the chair 7 or under the floor. The elastic material 8 may be made of any material and in any form including metal, rubber, silicone, polyurethane as long as it deforms in response to the amount of load.

Although there are provided examples of chair in FIGS. 4 to 6, the chaotic analysis can be conducted even when the sensor 3 is installed on the loading surface of the subject such as a bed, a floor, and the backrest of a chair. The prediction or determination of psychosomatic state of, for example, a patient in a hospital, or a driver or pilot of a vehicle such as an automobile and airplane can be made with the subject sitting down on a chair, or lying down on a bed, or standing still, without imparting any awareness to the subject.

When the time series signal of the load value or barycentric position is subjected to a chaotic analysis, the required sampling frequency of data is preferably in the range between approximately 10 Hz and 100 Hz, because the fluctuation of chaos in the load value or barycentric position resides in the low frequency band from 10 Hz to 100 Hz and the frequency components beyond the range can be considered as noises.

Accordingly, even when continuously monitoring the psychosomatic state, a relatively small number of samples may be sufficient, so that the amount of data will not be enormous. It should be noted that the chaos theory is a theory with the datum at a given point of time being used as an initial value, where an observation is made, on the data behavior of the sampled data at the next point of time, then on the sampled data at the succeeding point of time to thereby seek a dependency; the required data resolution of the load value or barycentric position is preferably approximately 8 bits to 16 bits or more because the prediction of chaos itself may significantly vary depending on the amount of noises convoluted on the data.

The noise elimination means 4 is a means operable to the signals of load value or barycentric position of the subject 6 for removing the noise components unnecessary for the calculation of the psychosomatic state exponent in the data processing means 20 mentioned above.

In the noise elimination means 4, in general, analog or digital low-pass or high-pass filters and the like are used to remove unwanted frequency components. Those frequency bands impossible in the chaos theory analysis, or noise components generated by the subject 6 when he/she sneezes, or noise components convoluted on the power line, are eliminated to thereby improve the precision of the data processing and the prediction or determination of the psychosomatic state.

The warning means 5 is a means for warning or notifying the subject 6 or the management station 9 that manages the subject 6 when the subject 6 is in the interval between the wakeful state and the non-wakeful state, or in an abnormal psychosomatic state.

The subject 6 can be warned through the warning means 5 to display the warning message on the display 11, or to sound a warning or an alert from the speaker 10.

In addition, it is possible not only to notify the management station 9 that controls and manages the subject 6 of the psychosomatic state of the subject 6 so as to thereby enable the management station 9 to manage the subject 6, but also to warn or direct the subject 6 directly from the management station 9 via a wireless communication and the like. The warning means 5 makes it possible to prevent an accident with certainly and before it happens due to a human error for example due to the dozing of the subject 6.

EXAMPLE 1

The operation of the psychosomatic state determination system 1 will be described in greater details with reference to the system configuration shown in FIG. 1. In the present example a case will be described in which the psychosomatic state of a subject 6 sitting on a chair 7 that has a sensor 3 built in thereto as shown in FIG. 6 is predicted or determined. In the present example the sensor 3 is an acceleration sensor.

Figure 7:
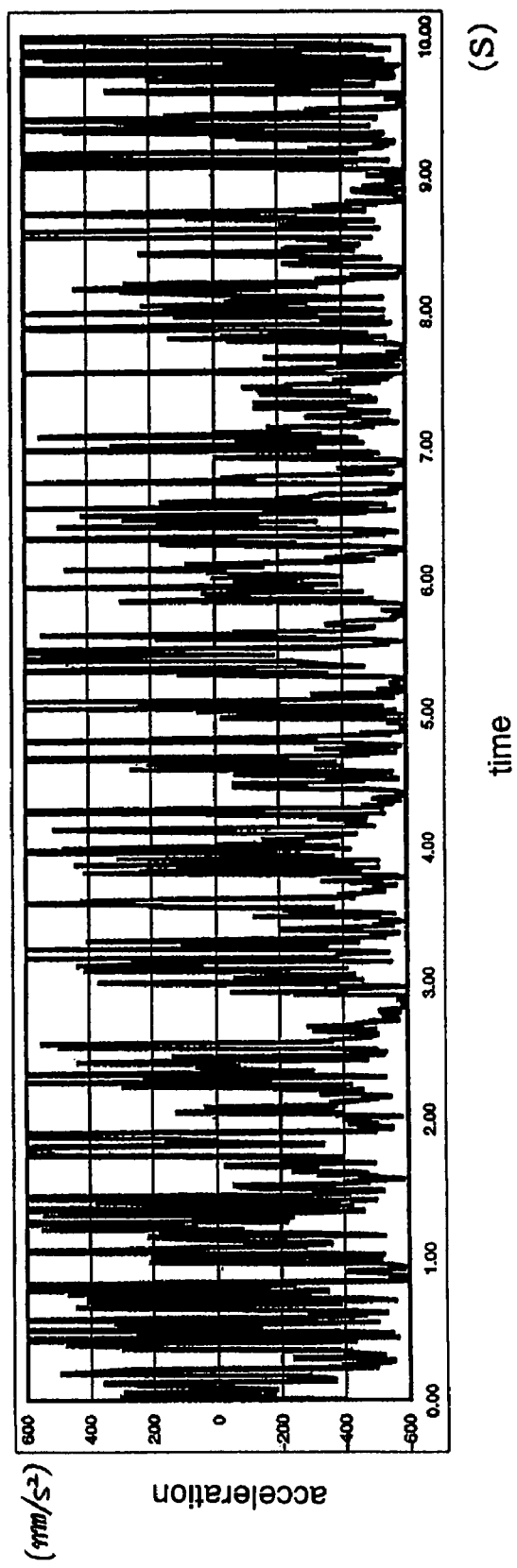
FIG. 7 shows a graph indicating the temporal change of output signals from the acceleration sensor attached to the chair.
Figure 8:
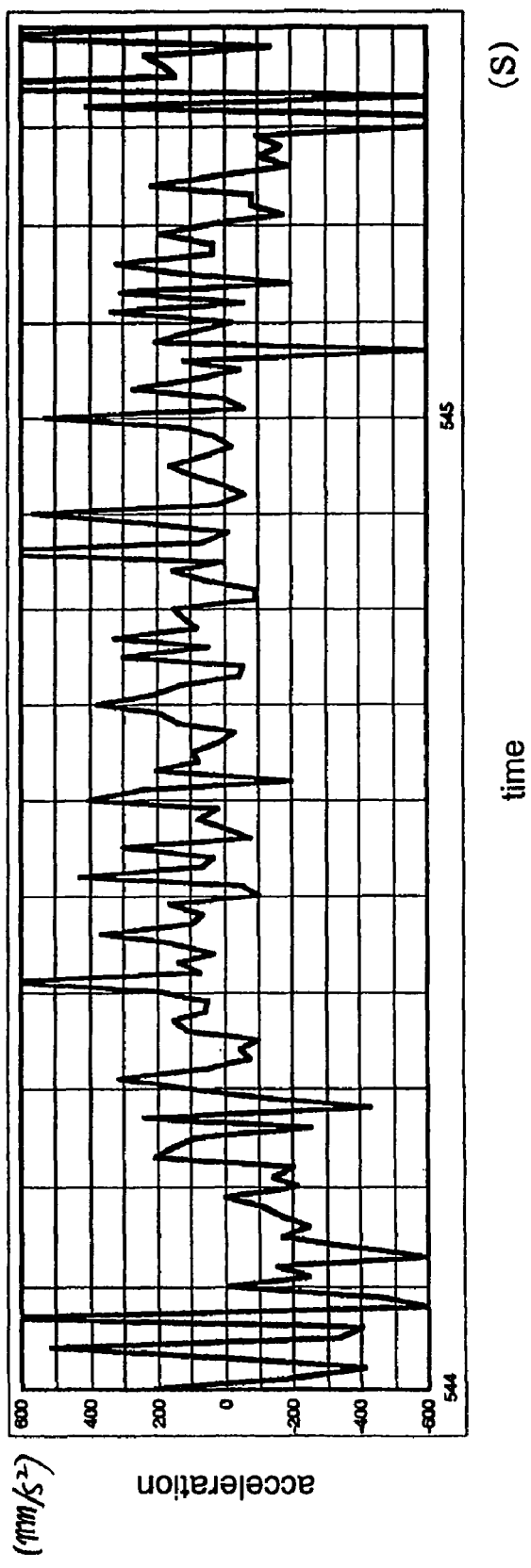
FIG. 8 shows another graph indicating the temporal change of output signals from the acceleration sensor attached to the chair.

First, the sensor 3 outputs the acceleration obtained from the subject 6 sitting on the chair 7, the output values are sequentially captured in the data processing means 20 in the order the earliest first in the time sequence. The time series data of the output values from the acceleration sensor in a given period of time is shown in FIGS. 7 and 8. FIG. 8 is an enlarged view of the time axis of FIG. 7 in a given period of time.

Figure 9:
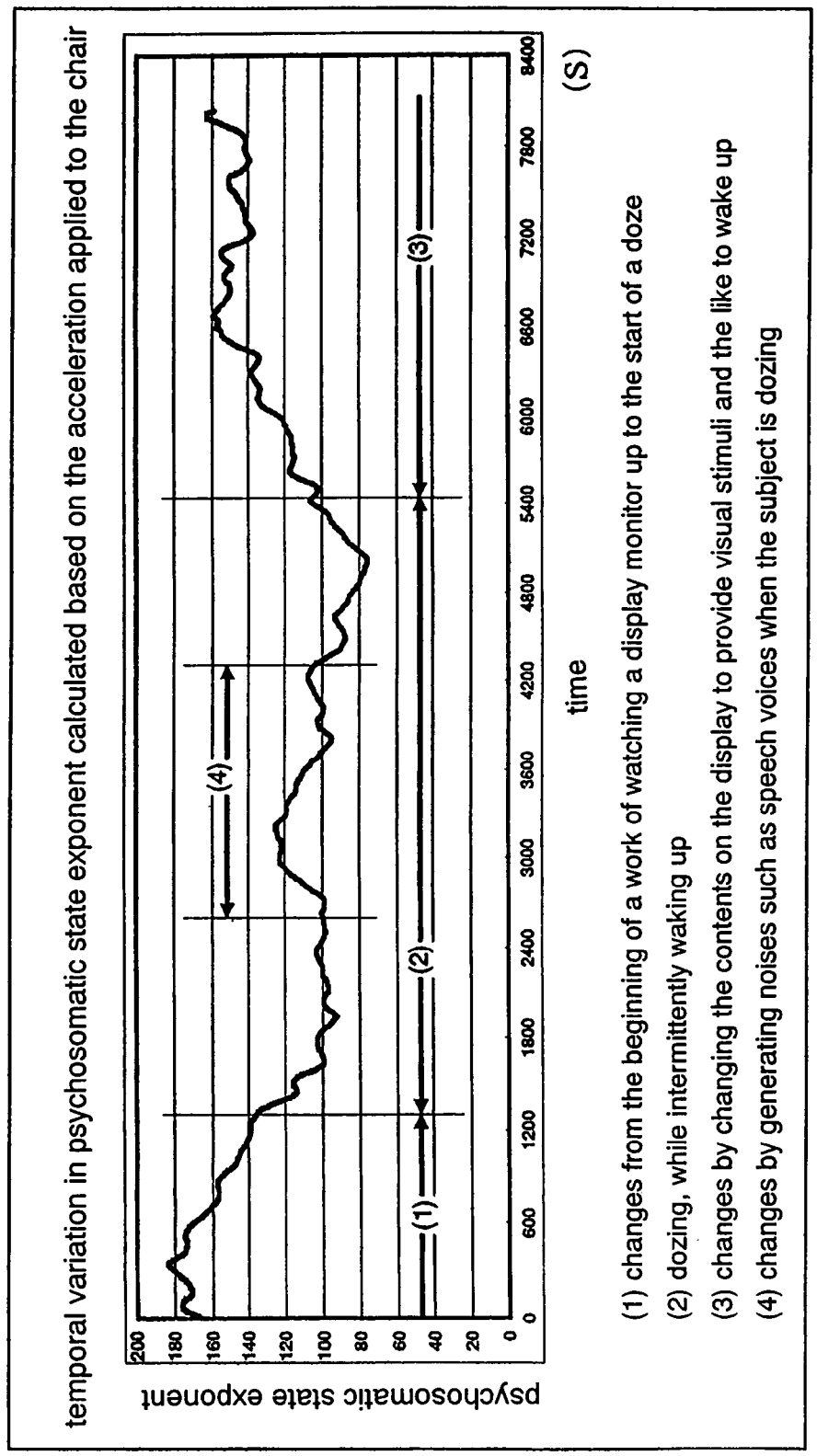
FIG. 9 shows a graph indicating the temporal change of psychosomatic state exponents.

Next, from the time series data, the psychosomatic state exponents are calculated in the data processing means 20. FIG. 9 shows the data of thus calculated psychosomatic state exponents versus time. It should be noted here that the psychosomatic state exponents shown in FIG. 9 are of cerebral function exponents, detailed calculation thereof will be described later.

In the evaluation means 22, the psychosomatic state exponents thus calculated is compared with the psychosomatic state exponents stored in the exponent database 24.

It will be appreciated that the psychosomatic state exponent does not increase as mentioned above in every situation even if the subject is tired. When the subject 6 sitting on the chair 7 and staying still as in the present example is considered, in case in which the subject is sitting in front of a radar scope in a flight control room, or is sitting in front of the operation console in a plant control room, if the subject becomes tired, the movement of barycentric position freezes and behaves like a mechanical motion, the psychosomatic state exponent calculated from the time series signal of the load value will gradually decrease as compared with the subject in a wakeful state, and the exponent will settle to a constant low value when he or she has completely fallen asleep.

As has been described above, the exponent database 24 in the present example stores the temporal tendency and/or a numerical value of the psychosomatic state exponent in correspondence with the psychosomatic state in such a way that, when the psychosomatic state exponent exhibits a temporal tendency that gradually drifts from higher to lower, a doze is predicted, and when the psychosomatic state exponent exhibits a certain value, it is determined to be a doze, in case the subject 6 is sitting on the chair 7.

Now considering the calculated psychosomatic state exponents as shown in FIG. 9, in the period (1) in the figure, the psychosomatic state exponent is higher at the beginning, indicating that the subject 6 is in a wakeful state and is doing a monitoring work of watching a display, however the psychosomatic state exponent gradually decreases, so that the prediction can be made that the subject 6 is in a semi-wakeful state just prior to a doze.

As at that time the subject 6 is not completely in a non-wakeful state, he or she is warned by the warning means 5 to thereby be brought back to a wakeful state to prevent an accident securedly and before it happens.

In the period (2) in FIG. 9, since the psychosomatic state exponents are generally stable at a lower level than in the wakeful state (1), it is determined that the subject 6 is dozing and is in a non-wakeful state.

The period (4) in FIG. 9 indicates that the subject is in the non-wakeful state similar to (2), however as the psychosomatic state exponent is momentarily and slightly increasing, it can be seen that although the subject 6 is dozing, due to noises such as speech voice or a warning sound or a call of cellular phone, the subject 6 is paying attention by his or her ears to the noise while dozing.

If the noise level is enough louder or some words relating to the subject 6 are spoken, the psychosomatic state exponent will further increase so that the subject 6 goes back to a wakeful state. However in FIG. 9, the noise level has been low and imparted only a few effects to the subject 6 so that it can be determined that the psychosomatic state exponent has settled again to a lower level and the subject 6 has gone back to a complete non-wakeful state.

In the period (3) of FIG. 9, as the psychosomatic state exponent has gradually increased to thereby go back to the value at the same level as (1), it can be predicted that the change of the display contents on the display in front of the subject 6 to impart visual stimuli to the subject 6 would bring back the subject 6 to a wakeful state and also it can be determined that the subject has gone back to a wakeful state.

In the present example, the output value from only one single acceleration sensor is used to predict or determine the psychosomatic state, and the prediction or determination of the psychosomatic state will be identical and similar results can be obtained even when more sensors are used, as long as the sensor 3 outputs the load value or barycentric position. It can be seen from the foregoing description that the present example makes it possible to predict or determine the psychosomatic state of a subject without imparting any awareness to the subject and without being based on any subjective determination.

The calculation method of a cerebral function exponent will be described in contrast to the calculation method of the conventional Lyapunov exponent.

The conventionally used Lyapunov exponent calculation method is based on the assumption that the dynamics (a fluctuation or a dynamic characteristic of a state along the time axis), of a system (a system; In the present example this is a system for measuring a time series signal of the load value or barycentric position obtained based on the psychosomatic state of the subject 6) is stable and in the conventionally used Lyapunov exponent calculation method, the main flow is to seek a neighborhood points set that satisfies a predetermined neighborhood condition (which is a set of points that have very proximal values or distances on a multi-dimensional space), and thereby to perform the convergent calculation with respect to that neighborhood points set. The convergent calculation is to track the behaviors of points in the neighborhood points set that at the beginning should be in mutually very close positions to follow their development afterwards, namely to observe the attractors, and this calculation is required for determining the chaoticity.

In case in which a plurality of dynamics are simultaneously convoluted, or the dynamics changes within a predetermined processing unit, such as the time series signal of the load value or barycentric position of the subject, the assumption that the dynamics is stable is not valid, so that thus calculated Lyapunov exponent has not always reliable.

In addition, since the time series signal of the load value or barycentric position have a short duration or repetition time in certain dynamics, and even if the conventional Lyapunov exponent is calculated for each of dynamics, the number of repetition of the convergent calculation is limited and the exponent has a value not always reasonable, and therefore the reasonableness is improved by averaging the values obtained in the period of approximately five minutes.

Because the calculation of conventional Lyapunov exponent assumes a generic time series signal including not only a periodic time series signal but also an aperiodic time series signal, if the processing unit is set longer, the seeking time of neighborhood points in the processing unit will be longer, while on the other hand the convergent calculation tends to unstable if the processing time is set shorter. Furthermore, the seeking time of neighborhood points will become longer by simply increasing the number of samples for the purpose of improving the precision of the convergent calculation. The optimization of parameters such as a processing unit and a neighborhood condition is difficult, as has been described above, and as a result of this, the calculation of conventional Lyapunov exponent hitherto has taken a longer time.

The calculation method of cerebral function exponent has been made in view of above circumstances and problems. More specifically, a quite convergent neighborhood points set is generated from the beginning, without specifying the processing unit or the neighborhood condition, by generating a set of candidate points of neighborhood points by using the stable range of period of the time series signal as the processing unit, in lieu of seeking the neighborhood points from within the processing unit of predetermined and fixed interval. Accordingly the process becomes faster and the local psychosomatic state exponent can be calculated stably and immediately even with the time series signal of a short duration of dynamics.

A generic methodology for observing attractors is, as similar to the calculation of the conventional Lyapunov exponent and the cerebral function exponent as will be described later, to generate a delay vector from the original time series signal and thereby to plot in the reconstructed state space. This is also referred to as the reconstruction of attractors. By observing these attractors, the information equivalent to the original system which created the time series signal can be observed. As a preliminary step before the description of calculation method of the cerebral function exponent, a simple example of attractor reconstruction will be described with reference to FIG. 10.

Figure 10:
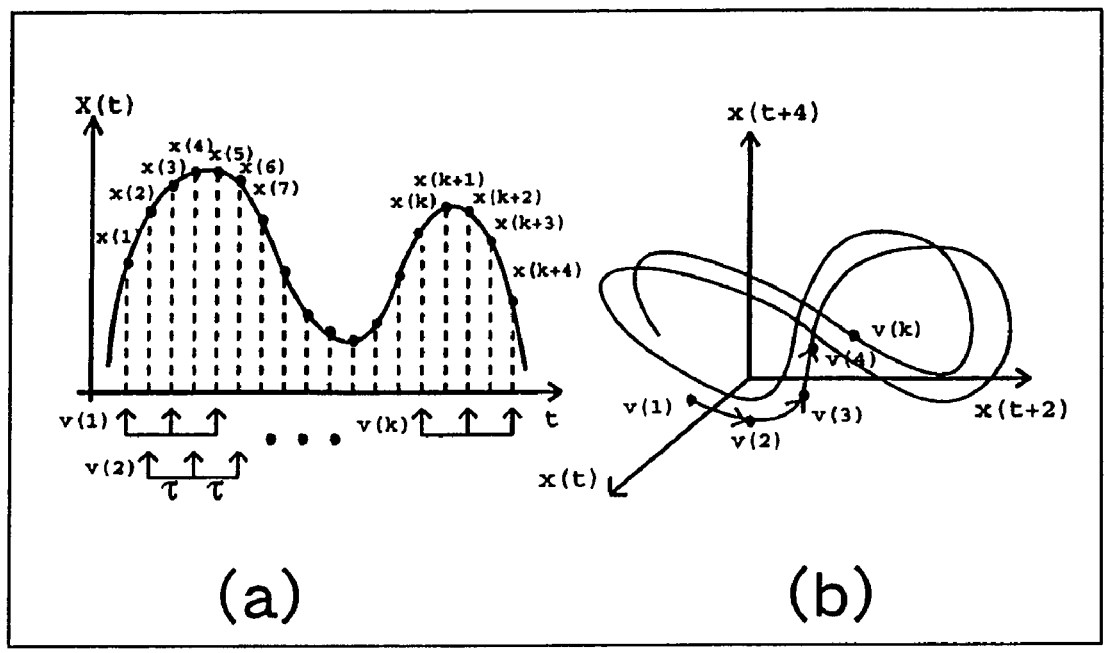
FIG. 10 shows an embodiment of reconfiguration of an attractor

Now define original time series signals as $\{x(1), x(2), x(3), \ldots\}$, an arbitrary signal from the components of the time series signals x is extracted to thereby create a time delay $\tau$, and a time delay vector in the m dimension $v(t)=\{x(t), x(t+\tau), \ldots, x(t+(m-1)\tau)\}$. The time delay vector $v(t)$ $\{i=1, 2, \ldots\}$ is plotted in the $m^{th}$ dimension space to thereby obtain the reconstructed attractor. In FIG. 10, the reconstruction of attractors is represented with time delay T=2, dimension m=3, and the left hand (a) in the figure shows the conversion of the time series signal into the time delay vector, and the right hand (b) shows the reconstruction of attractors by plotting the time delay vector into the time delay coordinate. When the dimension m is a dimension which can correctly represent the system information in which the original time series signal is obtained, m is called as an embedding dimension. If the attractor is reconstructed by the correct embedding dimension, then the evaluation of the chaoticity of the system can be conducted. It should be noted here that the condition where the conversion to the reconstruction state space using the time delay coordinate becomes embedded one has been proved by the embedding theorem of Takens and is known.

With reference to the foregoing generic description, the calculation method of cerebral function exponent will be described herein below. Now define the time series signal which is the base of the calculation of cerebral function exponent $s=s(t)$, as $s(t)=\{s_t|t=0, 1, \ldots\}$. $s(t)$ is time series signals with the output signal of the sensor 3 sampled at a constant sampling frequency f (Hz). The time interval between neighboring time series signals (for example, between s(1) and s(2)) is based on the sampling frequency $(1/f)(s)$.

Now define, as parameters in the chaos theory, an embedding dimension D, an embedding delay time $\tau_d$, an expansion delay time $\tau_e$, and a size of a neighborhood points set N. These parameters are also required to be defined when the conventional Lyapunov exponent is calculated.

The size of an neighborhood points set N has to be not less than the number of embedding dimensions D+1, and has to be set in accordance with the property of the time series signal. In order to stably conduct the following calculation without for example any zero-divide, it is preferable to set to D+2, D+3 or more. However, even if it is D+1, it will be possible to prevent the occurrence of zero-divide by performing dithering processing on the sampled time series signal. The dithering processing is an intentional addition of noise to the signal, and is common in the digital processing of audio signals. By performing a dithering processing, there are cases where the precision of restoring the digital signal to the original analog signal is improved.

When the dynamics changes in a continuous fashion, it is preferable to set the size N of neighborhood points set as small as the stable calculation is possible, in order to prevent points of different dynamics from being mixed into the neighborhood points set or into the set of points which are candidates of neighborhood points. For example, when the embedding dimension is 4, then the size N of neighborhood points set is preferably about 6 or 7.

For the embedding delay time $\tau_d$ and the expansion delay time $\tau_e$, values of integral multiple of the sampling period are selected, since these can be constructed from the point at which the time series signal is sampled.

In addition, the shortest period $T_m$ and the longest period $T_M$ of the time series signal is defined. Then, a set of time series signal x=x(i) that has a period T satisfying $T_m \leq T \leq T_M$ is cut out from the foregoing time series signal s(t) as the processing unit for cerebral function exponent calculation.

$$x(i) = \{x_i | i = 0, 1, \ldots, n_0\}, \quad \text{Equation 1}$$

where $n_0 = (D-1) \times \tau_d + (N-1) \times T_M + \tau_e$, and $$x(0) = x_0 = s(t_0).$$

As might be expected, there are cases where the period T is different depending on the cut out processing unit. The prediction of period T and the verification of whether the processing unit x(i) is a set satisfying the period T, are conducted by using any of frequency analysis methods such as a discrete Fourier transform (DFT), a linear prediction analysis (LPC) and a wavelet analysis. Not only the periodicity condition of whether or not it has the period T but only the condition in accordance with the magnitude of level (amplitude) of the sampled signal may be added to the cutting out of processing unit. For instance, a condition that the signal dynamic range is not less than a predetermined value may be added as the cut out condition of the processing unit.

Based on the definition as described above, an neighborhood points set $P = \{P_0, P_1, \ldots, P_{(N-1)}\}$ as shown by the following equation is created from within the determined processing unit x(i).

$$P_0 = (x_0, x_{\tau_d}, x_{2\tau_d}, \ldots, x_{(D-1)\tau_d}) \quad \text{Equation 2}$$

$$P_1 = (x_T, x_{\tau_d+T}, x_{2\tau_d+T}, \ldots, x_{(D-1)\tau_d+T})$$

$$\ldots$$

$$P_{(N-1)} = (x_{(N-1)T}, x_{\tau_d+(N-1)T}, x_{2\tau_d+(N-1)T}, \ldots, x_{(D-1)\tau_d+(N-1)T})$$

The neighborhood points set $P = \{P_0, P_1, \ldots, P_{(N-1)}\}$ shown in Equation 2 may also be defined as a set of points which are candidates of neighborhood points, where the components of x(i) are each sequentially put as the front element of $P_0$, $P_1, \ldots, P_{(N-1)}$, and the set is composed of a set of components where each front element has been sequentially delayed by time $\tau_d$.

When calculating the conventional Lyapunov exponent, as the periodicity of time series signal is not presumed, not surprisingly, the definition of period T as mentioned above is not defined, so that the processing units are sequentially cut out, at a predetermined and fixed unit of time, for example for every 10 ms. Accordingly, in case of the calculation of a conventional Lyapunov exponent, the neighborhood points set is not yet generated at that point of time, thus the process takes a longer time because the neighborhood points set that satisfies the predetermined neighborhood condition is searched for from within all of the sampled time series signals of the predetermined processing unit.

Next, the radius of a hypersphere which encloses the neighborhood points set P as mentioned above is defined as the neighborhood distance $\epsilon_s$, and it is given by the following equation:

$$\epsilon_s = \max\{\overline{P_0 P_1}, \overline{P_0 P_2}, \ldots, \overline{P_0 P_{(N-1)}}\} \quad \text{Equation 3}$$

The neighborhood distance $\epsilon_s$ is an essential parameter as the neighborhood condition when seeking an neighborhood points set in the calculation of the conventional Lyapunov exponent; however in the case of cerebral function exponent, this is not always needed to be used the neighborhood condition because an neighborhood points set or a set of candidate neighborhood points is already generated at that time.

In order to further increase the processing speed in the example, the neighborhood distance $\epsilon_s$ is used for the neighborhood condition having a meaning of screening the cut out processing units, and is also used as the condition of whether or not to continue the convergent calculation (a convergent calculation continuity condition) as will be mentioned later. There are cases where white noises, which should not have the original periodicity, are intensively included in the cut out processing units. In such a case, the neighborhood distance $\epsilon_s$ calculated for the processing unit that includes the white noise as one component has no chaoticity, so that it naturally takes a maximum value. In order to remove such a white noise as described above, the neighborhood condition may be applied, or the processing unit may be cut out by considering that a signal having a dynamic range of more than a certain value is not a white noise as has been described above.

In this example, the neighborhood condition is defined as $\epsilon_s < \epsilon_c$, and if the neighborhood distance $\epsilon_s$ of the neighborhood points set P as mentioned above does not satisfy this condition, then this P is considered not to be a neighborhood points set and the processing unit x(i) is rejected. Thereafter, another processing unit x(i') which has its origin at a point posterior to the processing unit x(i) in time sequence is newly generated, and the neighborhood points set P' generated from this x(i') is then determined whether or not to satisfy the neighborhood condition. It is to be noted that in case in which the processing units are not screened, this step may be omitted, and the processing units where every sampling points or arbitral sample points in the time series signal s(t) are used as respective origin may be generated to thereby apply the following calculation.

Next, when the neighborhood points set P as mentioned above satisfies the neighborhood condition, then the expansion delay time $\epsilon_e$ is applied to thereby generate the expansion points set S of the neighborhood points set P as follows. Note that $S_i$ is an expansion point corresponding to $P_i$.

$$S = \{S_0, S_1, \ldots, S_{(N-1)}\} \quad \text{Equation 4}$$

$$S_0 = (x_{0+\tau_e}, x_{\tau_d+\tau_e}, x_{2\tau_s+\tau_e}, \ldots, x_{(D-1)\tau_d+\tau_e})$$

$$S_1 = (x_{\tau_e+T}, x_{\tau_d+\tau_e+T}, x_{2\tau_d+\tau_e+T}, \ldots, x_{(D-1)\tau_d+\tau_e+T})$$

$$\ldots$$

$$S_{(N-1)} = (x_{\tau_e+(N-1)T}, x_{\tau_d+\tau_e+(N-1)T}, x_{2\tau_d+\tau_e+(N-1)T}, \ldots, x_{(D-1)\tau_d+\tau_e+(N-1)T})$$

The expansion points set $S=\{S_0, S_1, \ldots, S_{(N-1)}\}$ as shown in Equation 4 is composed of a set of elements where each component of neighborhood points set P is sequentially delayed by time $\tau_s$.

For the neighborhood points set P mentioned above, the displacement between the neighborhood point $P_0$ as reference and other neighborhood points $P_j$ is defined as follows. Furthermore, a similar displacement of the expansion points set S is also defined as well.

$$\vec{y}_j = \overrightarrow{P_0 P_j} = (x_{jT} - x_0, x_{\tau_d + jT} - x_{\tau_d}, \ldots, x_{(D-1)\tau_d + jT} - x_{(D-1)\tau_d})$$  Equation 5

$$\vec{z}_j = \overrightarrow{S_0 S_j} = (x_{\tau_e + jT} - x_{0+\tau_e}, x_{\tau_d + \tau_e + jT} - x_{\tau_d + \tau_e}, \ldots, x_{(D-1)\tau_d + \tau_e + jT} - x_{(D-1)\tau_d + \tau_e})$$

$j=1, 2, \ldots, N-1$

With respect to each displacement of the neighborhood points set P and the expansion points set S, if an estimated Jacobian matrix $A_0$ satisfying the following equation is obtained, then the cerebral spectrum, which is the base of a cerebral function exponent, can be calculated.

$$\vec{z}_j = A_0 \vec{y}_j, j=1, 2, \ldots N-1$$  Equation 6

Note that the calculation of cerebral spectra corresponds to the estimation of Lyapunov spectra in the conventional Lyapunov exponent.

The calculation of matrix $A_0$ will be conducted so as to satisfy the following equation:

$$S_0 = \sum_{j=1}^{N-1} |\vec{z}_j - A_0 \vec{y}_j|^2,$$  Equation 7

$$\frac{\partial S_0}{\partial a_0^{kl}} = 0,$$

where $a_0^{kl}$ is (k,l) element of $A_0$.

If the matrix $A_0$ has D dimensions, then D sets or more of the combination of micro-displacement vector $y_j$ and expansion displacement vector $z_j$, which are independent from one another and are not proportional, are required for the calculation of matrix $A_0$. When D sets or more of the combination of micro-displacement vector $y_j$ and expansion displacement vector $z_j$ are given, $S_0$ in Equation 7 provides the sum of square of errors in the relation between micro-displacement vector $y_j$ and expansion displacement vector $z_j$ when matrix $A_0$ is given. Therefore the partial differential of $S_0$ in Equation 7 means that the sum of square of errors in relation between micro-displacement vector $y_j$ and expansion displacement vector $z_j$ is minimum. In other words, Equation 7 describes that the matrix $A_0$ is estimated from the least square method.

Thus, a matrix $A_0$ can be given by the next equation.

$$A_0 = C_0 V_0^{-1}$$  Equation 8

$$(V_0)^{kl} \equiv \frac{1}{N-1} \sum_{j=1}^{N-1} y_j^k y_j^l$$

$$(C_0)^{kl} \equiv \frac{1}{N-1} \sum_{j=1}^{N-1} z_j^k y_j^l$$

If the matrix $A_0$ thus given can be QR decomposed ($A_0 = Q_0 R_0$), then the maximum value in the diagonal elements of the matrix $R_0$ is set to the cerebral function exponent corresponding to the time of the point $x_0$ earliest in the time sequence, among the time series signals forming the neighborhood points set P. Furthermore, when the diagonal elements of the matrix $R_0$ is sorted in a descending order, a cerebral spectrum having elements corresponding to the number of embedding dimensions can be obtained.

Basically, in case of the conventional Lyapunov exponent, even though it is calculated in correspondence with the time of $x_0$, because basically there are cases where different Lyapunov exponents are calculated based on the method of setting processing units, neighborhood conditions or reference points, the correlativity between local $x_0$ and its value is enough low so that there is no way other than increasing the reliability by averaging all Lyapunov exponents in the processing unit.

In contrast, the cerebral function exponent has a higher correlation between local $x_0$ and its value because the neighborhood points set is generated in synchronization to the periodicity of the time series signal.

In addition, following convergent calculation is performed to improve the reliability in the temporally local cerebral function exponent. Note that although the convergent calculation in the conventional Lyapunov exponent is essential as a means for verifying the validity of correlation between the neighborhood points set on which a search was previously made and its expansion points set, the cerebral function exponent, which has its very high validity of relationship between the neighborhood points set and its expansion points set, has an aim of calculation different from the convergent calculation in the conventional Lyapunov exponent.

In the convergence calculation, a new processing unit $x_1(i)$ is cut out which has a period T having the earliest point in the time sequence as an origin (namely, the first point $x_{0+\tau_e}$ of $S_0$) among time series signals that form the expansion points set S above. The number of components of $x_1(i)$ is $(n_0+1)$, similar to x(i) as mentioned above. This processing unit $x_1(i)$ is verified whether or not it satisfies the periodicity condition (whether it has a period T). For instance, if $x_1(n_0)$ is a signal not included in the period T, then the convergent calculation for the processing unit x(i) is terminated at that point of time.

If the processing unit $x_1(i)$ satisfies the periodicity condition, then an neighborhood points set P(1) from this $x_1(i)$, in a similar manner as above, is generated, and also similarly to the previous neighborhood points set P, if it satisfies the neighborhood condition and/or the convergence calculation continuity condition, then the expansion points set S(1) is generated from P(1). If, otherwise it does not satisfy the periodicity condition and/or the neighborhood condition, then it means that the dynamics has changed at that point of time, so that the convergent calculation ends. The end of calculation means that the cerebral function is calculated for each dynamics. By this, even if a plurality of different dynamics is simultaneously convoluted, the cerebral function exponents are calculated, one for each dynamics, namely as many as the number of dynamics.

In the nth convergent calculation, from within the time series signals forming the $(n-1)^{th}$ expansion points set S(n−1), the processing unit $x_n(i)$ with the earliest point in the time sequence as an origin is generated, then if this processing unit satisfies the periodicity condition, the neighborhood points set P(n) is generated, and if and only if the neighborhood points set P(n) satisfies the neighborhood condition as mentioned above, then the expansion points set S(n) is generated, in other words the convergent calculation will be continued.

Similarly to the procedure of determining $A_0$ with respect to the neighborhood points set P and the expansion points set S as mentioned above, a matrix $A_n$ denoting the correlation between a neighborhood points set P(n) and an expansion points set S(n) is determined. More specifically, $A_n$ can be given by the following equation.

$$A_n = C_n V_n^{-1} \quad \text{Equation 9}$$

$$(V_n)^{kl} \equiv \frac{1}{N-1} \sum_{j=1}^{N-1} y_j(n)^k y_j(n)^l$$

$$(C_n)^{kl} \equiv \frac{1}{N-1} \sum_{j=1}^{N-1} z_j(n)^k y_j(n)^l$$

Because the number of convergent calculations varies flexibly in accordance with the cut out processing unit and the neighborhood points set generated, unlike the convergent calculation by a certain number of times in the conventional Lyapunov exponent where the calculation is repeated without knowing whether or not the calculation has any meaning, and in this regard the calculation of cerebral function exponent contributes to speeding up the processing. The neighborhood condition and the convergent calculation continuity condition need not be uniform, and rather they can be varied depending on the number of convergence. For example, the neighborhood condition at the time of $n^{th}$ convergent calculation may be set in such a way that the calculated neighborhood distance $\epsilon_s$ is less than or equal to the neighborhood distance $\epsilon_x \times (n-1)$ of the neighborhood points set P(n-1) in the $(n-1)^{th}$ convergent calculation or less than or equal to $\epsilon_s \times (n-1) \times a$ (a is a constant, for example $a \leq 1.1$).

The cerebral spectrum $c = \{c_s | s=1, 2, \ldots, D\}$ with respect to the processing unit $x(i)$ having its origin $x_0$, at the time when the convergent calculation has proceeded to $n^{th}$, is expressed by the following equation with the time expansion matrix being M. The cerebral function exponent in the present example means the largest value in the cerebral spectra c. In other words, the cerebral function exponent corresponding to $x_0$ will be $c_1$.

$$M = \prod_{k=0}^{n} A_k = A_n A_{n-1} A_{n-2} \ldots A_1 A_0 = \quad \text{Equation 10}$$

$$A_n A_{n-1} A_{n-2} \ldots A_2 Q_1 R_1 R_0 = Q_n R_n R_{n-1} R_{n-2} \ldots R_1 R_0$$

$$c_s = \frac{1}{(n+1)(N-1)} \sum_{k=0}^{n} \log|R_k^s|$$

where $R_K^S$ is $s^{th}$ element in the diagonal elements of the matrix $R_K$ by counting in a descending order. The conventional Lyapunov exponent $\lambda_m$ corresponds to $c_s$; however $R_K^m$ in $\lambda_m$ means $m^{th}$ diagonal element of the matrix $R_k$.

Once the convergent calculation corresponding to the origin $x_0$ in the processing unit $x(i)$ and the calculation of cerebral spectrum and cerebral function exponent is finished, another processing unit $x(i')$ is cut out and then the convergent calculation corresponding to the origin $x_0'$ therewithin and the calculation of cerebral spectrum as well as the cerebral function exponent is performed in the same manner as above. Theoretically, if, for all sampling points, processing units each satisfying a certain periodicity condition originating from the sampling point thereof can be cut out, a cerebral spectrum with respect to the sampling point can be obtained; however it is not necessarily needed to calculate for all of the sampling points.

In case where a basically same behavior continues, for example the subject is sitting down and still on a chair, and where a specially high temporal resolution is not required in the measurement when compared to the case involving the conventional Lyapunov exponent, then the change in psychosomatic state can be visually grasped by making a time series graph of the result from the processing such as a temporally moving averaging, similarly to the conventional Lyapunov exponent.

Now a method of processing a cerebral function exponent for each of dynamics in order to make it easier to visually understand the change in psychosomatic state in greater details by calculating the cerebral exponent at a higher temporal resolution and at a higher precision when compared to the case in the conventional Lyapunov exponent will be described herein below.

Now let the cerebral function exponent and the like calculated for each processing unit cut out from the time series signal s(t) in the previous process to be a function CEm(t)={ $(c_m(T), \epsilon_s(T), T(t))|t=0, 1, \ldots$ } while letting it to correspond to the time t, the origin of the processing unit.

Note that $c_m(t)$ is the cerebral function exponent at time t (the time of origin of the cut out processing unit), $\epsilon_s(t)$ is the neighborhood distance which provided that cerebral function exponent, and T(t) is a period determined by the frequency analysis at the time cutting out of the processing unit. t is obviously the time based on the sampling period.

From the CEm(t), those for $t_0 \leq t \leq t_1$ are extracted to be set as CEm(t|$t_0 \leq t \leq t_1$). The period from $t_0$ to $t_1$ is the time during which a constant action continues, or the time during which the dynamics is approximately constant. For instance, this corresponds to a period of time of a specific constant action such as a period of time during which a driver drives a car at a constant acceleration on a straight road in the example 2 described later, and a period of time during which a subject lies on a bed in a fixed position. This is the continuous period of a phoneme comprised of a certain vowel. The Japanese language has a specific characteristic in each vowel.

The elements in CEm(t|$t_0 \leq t \leq t_1$) are then sorted in an ascending order depending on the size of $\epsilon_s(t)$ to thereby obtain CEm(i|$1 \leq i \leq n$).

From the CEm(i|$1 \leq i \leq n$), the cerebral function exponent $C_M$ for each of the action states is given by the following equation.

$$c_M^p(t|t_0 \leq t \leq t_1) = \frac{1}{i_{\varepsilon(p)}} \sum_{i=1}^{i_{\varepsilon(p)}} c_m(i) \quad \text{Equation 11}$$

where p is a numerical value meaning a ratio in percentage, $c_m(i_\epsilon(p))$ is the $(n \times p)^{th}$ element. For example, if p=10%, then the elements of first 10% of CEm(i|$1 \leq i \leq n$) (elements in an ascending order in size until the number of elements reaches 10% of the total number of elements), are extracted, and then the mean value of these extracted elements $C_m(i)$ will be the cerebral function exponent $C_M$ corresponding to each of the action states. FIG. 9 used in the preceding example shows a graph after a temporal moving averaging is applied to thus obtained cerebral function exponent $C_M$.

However, when the period $t_0 \leq t \leq t_1$, or the period of a constant action is long as in the present example, the psychosomatic state during the period is changing even if the dynamics is not so significantly varied, resulting in a hindrance to the instant prediction or determination of the psychosomatic state. Therefore the period $t_0 \leq t \leq t_1$ is only necessary to be segmented to a degree such that the change in the psychosomatic state becomes traceable, to thereby calculate a cerebral function exponent $C_M$ for each of those segmented periods of time (the number of samples being in the order of approximately 1000 or so). It is needless to say that when the psychosomatic state changes, either the periodicity of the time series signal varies or does not satisfy the neighborhood condition and thus the convergent calculation conducted up to that point of time is aborted at that point of time, so that the time of change of the psychosomatic state or the time of change of the dynamics will be the extraction timing of CEm ($t|t_0 \leq t \leq t_1$).

It is preferable to vary p in accordance with the measurement precision of the time series signal obtained from the sensor 3, or in accordance with the conversion performance at the time when an analog time series signal is converted to digital signals. It is preferable to set p to about 10 to 20% for a signal where the noises irrelevant to the chaos has been sufficiently eliminated by the noise elimination means 4, or a signal having a large dynamic range because of a high performance of the sensor 3 and the A/D (analog-to-digital) converter. On the other hand, for a signal having a high noise level caused by either the sensor 3 or A/D converter which has a poor performance, it is preferable to set p to not less than 30%.

When using the cerebral function exponent $C_M$ in the psychosomatic state determination system of the present invention, if a relatively high resolution on the time domain is not required with respect to the temporal tendency, in other words a high resolution is not needed, then the cerebral function exponent $C_M$ can be calculated also as follows. First, based on the size of $\epsilon_s$, the CEm ($t|t_0 \leq t \leq t_1$) is given by the following equation from the elements ($c_m(T)$, $\epsilon_s(t)$, $T(t)$) forming the CEm ($t|t_0 \leq t \leq t_1$).

$$CEm(r;t|t_0 \leq t \leq t_1) = \{(c_m(t), \epsilon_s(t), T(t)) | \epsilon_s < r; t_0 \leq t \leq t_1\} \quad \text{Equation 12}$$

The cerebral function exponent $C_M(t|t_0 \leq t \leq t_1)$ for the CEm($t|t_0 \leq t \leq t_1$) can be given by the following equation, with respect to the SiCECA neighborhood distance $\epsilon_s(t)$.

$$c_M^r(t|t_0 \leq t \leq t_1) = \frac{1}{N_r}\sum^{N_r}(c_m | c_m \in \underline{CEm}(t|t_0 \leq t \leq t_1)) \quad \text{Equation 13}$$

where r is the percentage of the SiCECA neighborhood distance $\epsilon_s$ with respect to the radius of the strange attractor constructed in a embedding space, $N_r$ is the number of elements, among $C_m \in C_M(t|t_0 \leq t \leq t_1)$ satisfying the condition that $\epsilon_s$ is less than or equal to 10% of the radius of the strange attractor at the time when $c_m$ is given.

For instance, $C_M^{10}(t|t_0 \leq t \leq t_1)$ is given by extracting elements, from within elements of CEm($t|t_0 \leq t \leq t_1$) that are less than or equal to 10% of the radius of the strange attractor at the time when $c_m$ is given by $\epsilon_s$, then it is given as a mean value of the values of elements $c_m$ thus extracted. Unlike $C_M^p$ as mentioned above, in case of $C_M^r$, which is given as a mean value of $c_m$ in which $\epsilon_s$ is less than or equal to 10% of the radius of the strange attractor, the number of elements to be extracted is not defined by r, rather it varies depending on the time when $C_M$ is given.

Although $C_M^r$ may be mechanically calculatable for an arbitrary r where $0\% < r \leq 100\%$, r is required to be set to $r \leq 10\%$ in order to more correctly predict or determine the psychosomatic state, since the changing rate abruptly decreases when $r > 10\%$ if the time series signal to be processed has a strong chaoticity such as in case of the time series signal of a load value or a barycentric position or a speech voice.

In a similar manner to the calculation of $C_M$ using P, $C_M$ that is calculated by using r is given as the mean value of $c_m$. Accordingly, when $i_{\epsilon(p)}$ in equation 11 is smaller, or $N_r$ in equation 13 is smaller, the precision of $C_M$ decreases. Thus r is required to be set to not less than 2% or 3%.

The storage medium which stores any variables, equations, and values necessary for the calculation of cerebral function exponent, and which further stores the instructions for calculation processing of these variables, equations and values in the four-function calculation, integrodifferential, functions, arrays, pointers, branching, repetition, reentrant process, based on the calculation method of cerebral function exponents as have been described above constitutes a cerebral function exponent calculation program. The cerebral function exponent calculation program is executed by a generic computer comprised of any hardware such as a memory, processor and storage means, and can be a component of the data processing means 20.

EXAMPLE 2

Figure 2:
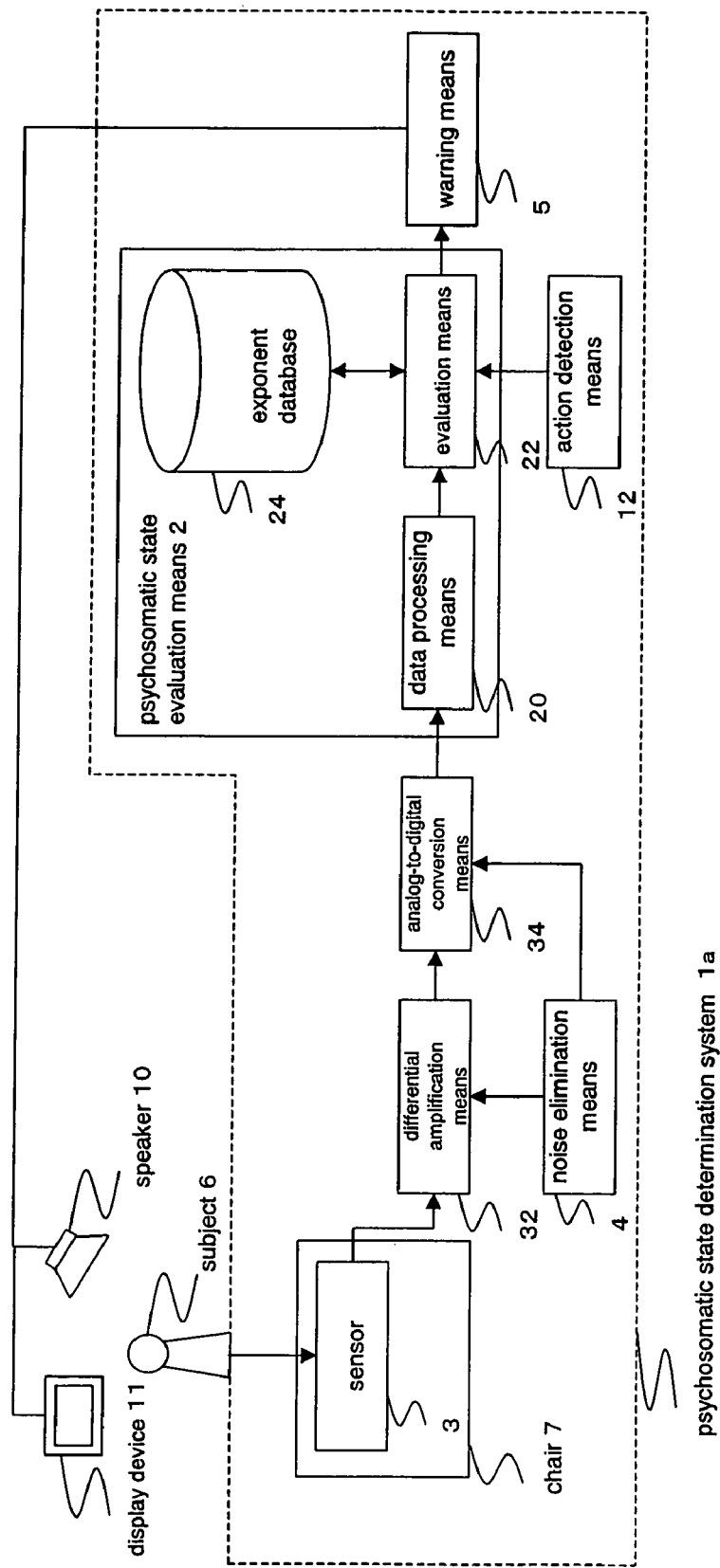
FIG. 2 shows another exemplary system configuration of the psychosomatic state determination system in accordance with the present invention.

In the present example, an exemplary configuration of the psychosomatic state determination system for predicting or determining the psychosomatic state of a subject riding on a vehicle (i.e., the subject is moving) with two or more sensors being attached to the sitting surface or backrest of a chair of the vehicle will be explained. An example of the psychosomatic state determination system in such a configuration is shown in FIG. 2.

The psychosomatic state determination system 1a includes a psychosomatic state evaluation means 2, a sensor 3, a differential amplification means 32, an analog-to-digital converter means 34, a noise elimination means 4, a warning means 5, and an action detection means 12. The psychosomatic state evaluation means 2, sensor 3, and warning means 5 are identical to those explained above and will not be explained.

The noise elimination means 4 is a means, similar to that described in the preceding example 1, for eliminating any unwanted noise components. However, when the subject 6 is riding a vehicle, as is the case of present example, the vibration component and the like of vehicles transiently generated by running on a dirt road or by starting the engine, is convoluted on the signal data obtained from the sensors 3 as noises, so that the elimination of such noises caused by the vibration and the like is essential.

In case of the signals obtained from the sensors 3, at least the frequency components above or equal to the sampling frequency can be cut off by sampling, but because the noise component due to the surface irregularity of a road is in relatively lower frequencies, the noise component can be eliminated by eliminating or attenuating a specific frequency band by using a band elimination filter and the like, or by providing a sensor different from sensor 3 for measuring the biological signal of a subject 6 to thereby subtract the pure noise component of obtained therefrom by the differential amplification means 32 to be explained in the following stage.

The differential amplification means 32 is a means for amplifying the output signal from the sensor 3. For example, when a pressure-sensitive resistor element is used for the sensor 3, the output resistance of the pressure-sensitive resistor element is inserted to the input stage of the differential amplification means 32 to thereby obtain an electric signal corresponding to the magnitude of pressure. Providing this means can facilitate the data processing by amplifying very small time series signal of the load value or barycentric position.

For the chair 7 having a plurality of sensors 3 as shown in FIG. 4, the differential amplification means 32 is also a means for specifying the barycentric position from the load value which is a measured output signal from each sensors 3.

For example, in case that the output of the sensor 3 is an electric signal, the barycentric position can be obtained by calculating the potential difference of the signal output from the sensor 3 to thereby compare to find the location of the highest potential in the differential amplification means 32.

The position of and the number of sensors 3 for identifying the barycentric position can be arbitrarily defined. Regardless of the positions of and the number of sensors 3, the time series signal of the barycentric position calculated exhibits a chaotic behavior. Thus, it is not always necessary to provide a number of sensors 3 in a matrix form; rather at least two sensors 3 are sufficient for the calculation of barycentric position. The deployment of sensors 3 in a matrix form is not required, so that the introduction of the psychosomatic state determination system 1 is facilitated and provides a merit in the cost. If, on the contrary, a number of sensors 3 are used, the output delay intrinsic to each sensor 3 is different and will affect the chaotic analysis unless the delay is identical among sensors 3. It is thus preferable to use less number of sensors.

The analog-to-digital conversion means 34 is a means for converting to a digital signal to be processed in the data processing means 20 to thereby obtain time series signals, when the amplified signal in the differential amplification means 32 is an analog signal. To convert an analog signal to a digital signal, the sampling and quantization as mentioned above may be done in this analog-to-digital conversion means 34.

The action detection means 12 is a means for detecting in a time sequence the operating state or the driving state of the subject 6. For example, the load value or the barycentric position will be different according to the behavioral states, whether the individual is sitting still on a chair, or standing still, or driving a vehicle. Thus, the temporal tendency and the value of the psychosomatic state exponent will vary even if the psychosomatic state is the same.

The case when driving a vehicle can be classified to either the case when the vehicle is standing still and the case when the vehicle is running. When the vehicle is running, the acceleration state and the barycentric position change in correspondence with the curve, the change of direction such as right or left turn, or acceleration. It is therefore required to detect the operating state of the acceleration sensor, brake or steering by the action detection means 12 to thereby grasp the driving state.

Especially when predicting or determining the psychosomatic state of the subject 6 who is driving a vehicle, a minute delay significantly affects the prediction of a chaos. Therefore it is preferable that the time series data of the state obtained in the action detection means 12 and the time series data of the barycentric position obtained from the sensor 3 are synchronized with each other, to thereby avoid any delay.

An exemplary operation of the present example will be described in greater details with reference to the system configuration of the psychosomatic state determination system 1a shown in FIG. 2.

In the psychosomatic state determination system 1a, the pressure signals, indicative of the load state of the subject 6 and received in the sensors 3, are transduced to electric signals, from which in turn any unwanted frequency components are eliminated in the noise elimination means 4; the barycentric position of the subject 6 is determined by a processing in the differential amplification means 32; the time series signal of the barycentric position is converted to digital time series signals in the analog-to-digital converter means 34; and the psychosomatic state exponent is calculated in the data processing means 20.

The exponent database 24 stores a temporal tendency and/or a value of a known psychosomatic state exponent corresponding to a psychosomatic state for each operating condition or driving condition of the subject 6; the known psychosomatic state exponent in the detected state of the subject 6 in the action detection means 12 is compared with the psychosomatic state exponent already calculated in the evaluation means 22. By doing this, the prediction or determination of the psychosomatic state can be sequentially conducted, according to the situation where the subject 6 is in.

For instance, when a driver of a vehicle is in a fully wakeful state, the individual accepts through eyes and ears various external information and senses the information with respect to the road condition via the chair; the individual pays attention to the instrument panels and sceneries, and as a result the trace of the barycentric position of the body of the individual corresponds to the changes in the necessary changes of the body posture; even when acceleration is applied, the individual can predict the occurrence of acceleration by the visual information, so that the individual can cope therewith by a stable barycentric displacement with less loss.

Thus, in case of a driver in a fully wakeful state, the changes in the barycentric position in corresponding to the acceleration and road conditions are stable, and the value of psychosomatic state exponent decreases.

On the other hand, in case of a driver in a fatigue state, the brain does not accept any external information; in a flat and plain drive such as running on a straight road, the trace of the barycentric position becomes simple and the value of psychosomatic state exponent decreases. However, when acceleration is applied or passing a corner, the body response delays, causing unnecessary movements to increase to thereby cause the barycentric position to become unstable, resulting in that the value of psychosomatic state exponent then increases.

As has been described above, the temporal tendency or value of the psychosomatic state varies depending on the operation condition or the driving conditions of the subject 6 even when his/her psychosomatic state is the same; to predict or determine the psychosomatic state of a driver riding on a vehicle, a database is provided for each state to be detected in the action detection means 12 to thereby compare the calculated psychosomatic state exponent with psychosomatic state exponents known for the operation or driving conditions at that time and then to predict or determine the psychosomatic state.

When obtaining a cerebral function exponent as a psychosomatic state exponent, the change in the operation or driving states causes basically a change in the periodicity; the cutting out of processing units and the convergent calculation will be aborted at the time when the periodicity changes. Accordingly the cerebral function exponent can be obtained for each operation state, namely for dynamics. In addition, because the cutting out of the processing units is performed based on the periodicity of the time series signal, the cerebral function exponents can be each calculated for each dynamics, namely as many as the number of dynamics, even when a plurality of different dynamics are simultaneously convoluted.

The calculation method of the cerebral function exponent is such as described in the preceding example 1. From within the CEm(t) obtained previously, those for $t_0 \leq t \leq t_1$ are extracted to be set to $CEm(t|t_0 \leq t \leq t_1)$.

In the present example, the period $t_0$ to $t_1$ is a period where a constant action is maintained as detected in the action detection means 12, and can be separated into, for example, a period of running on a straight road at a constant acceleration, a period of standing still, a period of turning a curve, and the like.

If the period $t_0 \leq t \leq t_1$, in other words the period of constant action is as long as seen in the preceding example 1, the psychosomatic state, of course, is changing during the period, and this will adversely affect the instant psychosomatic state prediction or determination. Accordingly, the period $t_0 \leq t \leq t_1$ should be segmented into finer fractions to such a degree that the changes in the psychosomatic state can be traced, to thereby calculate the cerebral function exponent $C_M$ for each of thus segmented fractions of the period.

EXAMPLE 3

In the present example, a psychosomatic state determination system will be described in which the subject is intentionally stimulated thereby to predict or determine the psychosomatic state of the subject. The system configuration of the psychosomatic state determination system in accordance with the example is shown in FIG. 3.

Figure 3:
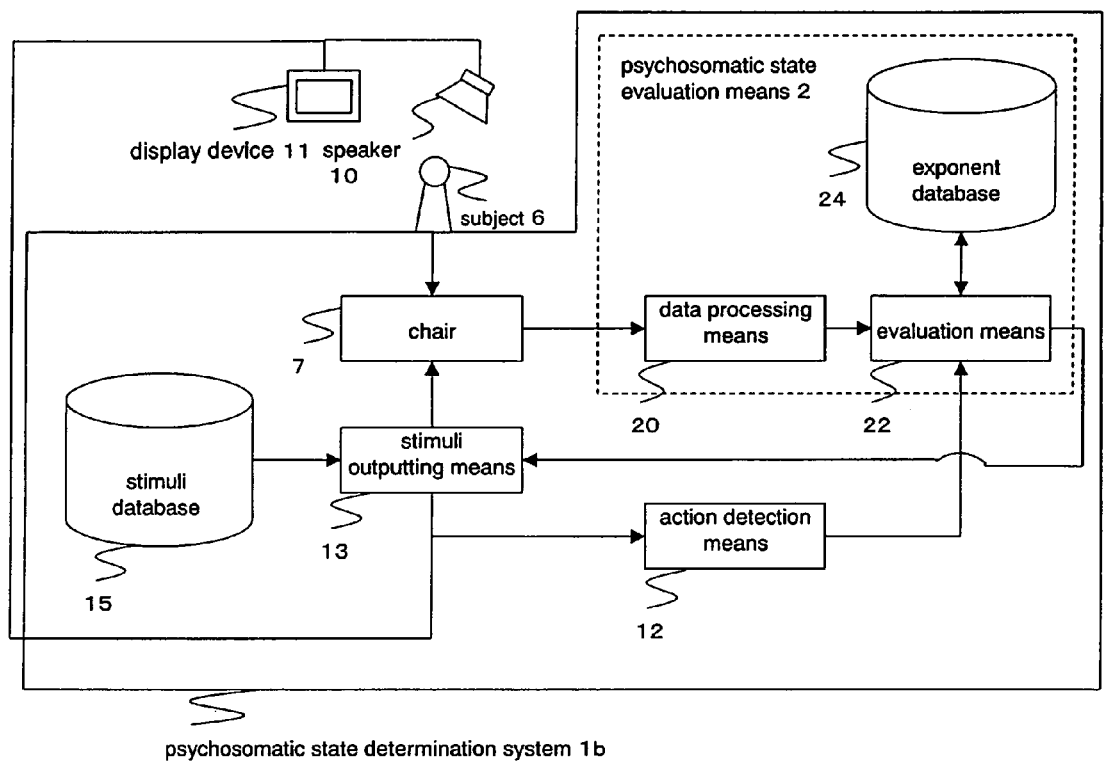
FIG. 3 shows still another exemplary system configuration of the psychosomatic state determination system in accordance with the present invention.

The psychosomatic state determination system 1b shown in FIG. 3 comprises, in addition to the system components of the psychosomatic state determination system 1a shown in FIG. 2, a stimulation output means 13 and a stimuli database 15.

The stimulation output means 13 is a means for stimulating the subject 6. For example, the means vibrates the chair or bed having the sensors 3 built-in, or stimulates visually or acoustically.

A specific example of the stimulation output means 13 includes a pressure sensor such as a piezoelectric element. The pressure sensor can transduce not only the pressure into an electric signal but it can transduce also the electric signal into a pressure, i.e., vibration or swing, so that another sensor can be placed in the vicinity of the sensor 3 to thereby provide a predetermined and intentional vibration.

The stimulation output means 13 may be any of means capable of controlling the vibration by a computer and the like to output the vibration, being other than a piezoelectric element. The acoustic stimulation can be provided by sounding a music or speech through a speaker 10, while the visual stimulation is provided by displaying a still image or motion picture on a display device 11.

The stimuli database 15 is a database for storing the vibrations, voices and images to be output in the stimulation output means 13.

Now an exemplary operation of the present example will be described in greater details with reference to the system configuration of the psychosomatic state determination system 1b shown in FIG. 3.

The exponent database 24 stores previously known data, where, when a vibration A, for example, which is stored in the stimuli database 15, is applied to a non-wakeful subject, a temporal tendency or value B of psychosomatic state is given, and the vibration A, for example, is applied to a wakeful subject, a temporal tendency or value C of psychosomatic state is given. The correspondence between the psychosomatic state and the psychosomatic state exponent should be explicitly and previously identified, for each of the types of stimulation including the vibration as well as the music and images.

For example, when a constant micro-vibration is applied to the subject 6, the brain of the subject 6 in a wakeful state, which has the information processing capability to respond to the micro-vibration, will follow the micro-vibration without any significant delay to displace the barycentric position. The subject 6 in a fatigue state, however, is slow to respond to the micro-vibration so that the change in the barycentric position in response to the micro-vibration will be delayed. If the subject 6 is more tired, the response will further slow down and ultimately exhibits an excessive response to the micro-vibration to loose the barycentric position stability.

While the subject 6 is listening to a rhythmic hot number, and if he or she feels better, then he or she will respond to the rhythm to shake his or her body; if he or she does not feel good he or she does not respond to the rhythm. The difference will be shown in the difference of the value or temporal tendency of the cerebral function exponent.

As has been described above, the psychosomatic state of the subject 6 can be predicted or determined by intentionally supplying stimuli to the subject 6, calculating the cerebral function exponent, then comparing it with the temporal tendency or value of the known cerebral function exponent.

Next, the psychosomatic state determination system used for supplying physical stimuli or audiovisual stimuli so as to facilitate the recovery from an abnormal psychosomatic state to the normal psychosomatic state in case in which the subject is predicted or determined to be in an abnormal psychosomatic state such as dozing, will be described in greater details with reference to FIG. 3.

If it is known in advance that the cerebral function exponent goes back to the value of wakeful state when supplying certain stimuli such as the music, image, and vibration to the subject in doze or likely to doze, then the music, image or vibration can be output from the stimulation output means 13 based on the psychosomatic state of the subject 6 predicted or determined in the evaluation means 22 at the time when the state of the subject 6 prior to dozing is predicted, so that the system helps preventing the subject 6 from falling into an abnormal psychosomatic state, or promoting changes in behavior of the subject 6.

Since the supply of stimuli to the subject 6 is also detected by the action detection means 12, the change in the psychosomatic state in that condition (condition that a stimulus is given) can be also continuously observed. If the subject 6 does not yet recover from the state where he or she is likely to doze, then the system will responsively supply larger stimuli.

Since the prediction or determination of psychosomatic state can be done by intentionally supplying stimuli to the body of subject 6, and at the same time this can help preventing the subject 6 from falling into an abnormal psychosomatic state or promoting changes in behavior of the subject 6, the psychosomatic state determination system in accordance with the example is preferable for avoiding an unnecessary warning or an intimidation to the subject 6 as well as for conducting a psychological test to the subject 6.

It should be noted that in case of each means and database in accordance with the present invention, its functionality is only separated logically, and may share physically or practically the same field. It is also needless to add that a data file may be used instead of a database, and that the term database should be considered to include the data file.

In the implementation of the present invention, the system of the embodiments may be realized by providing a recording medium which stores a software program for realizing the functions of the preferred embodiment to the system, then by reading the program stored on the recording medium from the computer in the system to thereby execute thereon.

In such a case the program itself read from the recording medium realizes the functionality of the preferred embodiments described above, and the recording medium which has stored the program thus constitutes the present invention.

The recording medium used for supplying the program may include, for example, magnetic disks, hard disks, optical disks, magneto-optic disks, magnetic tapes, non-volatile memory cards and the like.

The functionality of the embodiments as mentioned above may be realized by executing the program read by the computer, while the operating system and the like running on the computer performs part or all of the actual processing based on the instruction provided by the program, and the functionality of the embodiments realized by the processing may also be included in the present invention.

INDUSTRIAL APPLICABILITY

The present invention makes it possible to predict or determine the psychosomatic state of a subject without imparting any burden or awareness to the subject, without being based on any subjective decision; the present invention not only determines that the subject "has fallen asleep" but also predicts that the subject is "likely to fall asleep", and is able to warn prior to falling asleep, and the present invention therefore may any accidents caused by human errors, with certainty and before it happens.

Using at least one sensor which is implementable in the seating surface or backrest and the like of a chair, enables the prediction or determination of the psychosomatic state of a patient in a hospital, or a driver or a pilot driving or steering a vehicle or an airplane and the like, without imparting any awareness. Since only one single sensor nay be sufficient, there is an advantage that the synchronization among sensors or the difference among individuals due to the output delay present mutually among sensors are not needed to be considered, and that less number of parts is required.

In addition, at least two sensors are sufficient even for measuring the barycentric position, and the placement of a number of sensors in a matrix form is not needed, facilitating the installation of apparatus along with the merit of the cost reduction.

The intentional supply of direct stimulation to the body of the subject or audiovisual stimulation allows the prediction or determination of the psychosomatic state of the subject at that time, as well as the prevention of the individual from falling into an abnormal psychosomatic state, or the promotion of the changes in behavior of the subject; the present invention is effectively applied to avoid an unnecessary warning or intimidation, or to conduct a psychological test.

What is claimed is:

1. A system for determining a psychosomatic state of a subject, the system comprising:
    data processing means for:
        identifying, from a time series signal representative of the movement of the subject, a plurality of processing units each comprising a portion of the time series signal, the identification of the processing units being based on periodicity of the time series signal; and
        calculating psychosomatic state indicators for the plurality of processing units; and
    evaluation means for:
        making a comparison of a temporal tendency of the calculated psychosomatic state indicators with a temporal tendency of known psychosomatic state indicators stored in a database, the temporal tendency of known psychosomatic state indicators corresponding to a known psychosomatic state; and
        indicating a determined psychosomatic state of the subject based on the comparison.

2. The system according to claim 1, further comprising at least one sensor for providing the time series signal.

3. The system according to claim 2, wherein the sensor comprises at least one of a pressure sensor, a pressure-sensitive resistor element and a potentiometer, or an acceleration sensor.

4. The system according to claim 2, wherein the sensor comprises a sensor attached to one of a chair or a bed to which a load of the subject is applied.

5. The system according to claim 4, wherein the sensor comprises a sensor attached to one of a chair or bed having an elastic material therein, wherein the elastic material is chosen from metal, rubber, silicone, and polyurethane.

6. The system according to claim 1, further comprising noise elimination means for eliminating an unwanted frequency component included in the time series signal.

7. The system according to claim 1, wherein the system extracts samples from the time series signal at a rate of from 10 Hz to 100 Hz.

8. The system according to claim 1, further comprising amplifying means for amplifying the time series signal.

9. The system according to claim 2, wherein:
    the sensor comprises a plurality of sensors outputting a load value; and
    the system further comprises calculation means for calculating a barycentric position of the subject from each of the load values.

10. The system according to claim 1, further comprising warning means for sounding an alarm by using at least one of a display or a speaker to the subject.

11. The system according to claim 1, further comprising action detection means for detecting, in time sequence, at least one of an operation status or a driving behavior of the subject,
    wherein the evaluation means compares a temporal tendency of the known psychosomatic state indicators corresponding to a status detected in the action detection means and a psychosomatic state with a temporal tendency of the calculated psychosomatic state indicators to thereby determine a psychosomatic state for the subject.

12. The system according to claim 1, further comprising stimuli outputting means for giving to the subject a stimulus comprising at least one of a physical stimulus or an audiovisual stimulus,
    wherein the evaluation means compares a temporal tendency of the known psychosomatic state indicators, at a time when the stimulus is output, with a temporal tendency of the calculated psychosomatic state indicators to thereby determine the psychosomatic state of the subject.

13. The system according to claim 12, wherein the stimuli outputting means promotes a change in the behavior of the subject by outputting the stimulus based on the determined psychosomatic state, wherein the stimulus is effective for preventing the subject from falling into a non-wakeful state.

14. The system according to claim 1, wherein the psychosomatic state indicators are chosen from a Lyapunov exponent and a cerebral function exponent.

15. The system according to claim 3, wherein the sensor comprises a piezoelectric pressure-sensing element.

16. The system according to claim 5, wherein the elastic material comprises metal in a shape of a spring.

17. The system according to claim 2, wherein the sensor is one single unit.

18. The system according to claim 1, further comprising means for communicating the determined psychosomatic state of the subject to an administration station which manages the subject.

* * * * *